US012648990B2

(12) United States Patent
Wang et al.

(10) Patent No.: US 12,648,990 B2
(45) Date of Patent: Jun. 9, 2026

(54) BACTERIAL MEMBRANE VESICLES, AND SEPARATION AND PREPARATION SYSTEM AND METHOD THEREFOR

(71) Applicant: Sichuan University, Chengdu (CN)

(72) Inventors: Zhenling Wang, Chengdu (CN); Yuquan Wei, Chengdu (CN)

(73) Assignee: Sichuan University, Chengdu (CN)

( * ) Notice: Subject to any disclaimer, the term of this patent is extended or adjusted under 35 U.S.C. 154(b) by 958 days.

(21) Appl. No.: 17/637,051

(22) PCT Filed: Sep. 19, 2019

(86) PCT No.: PCT/CN2019/106654
§ 371 (c)(1),
(2) Date: Aug. 12, 2022

(87) PCT Pub. No.: WO2021/031270
PCT Pub. Date: Feb. 25, 2021

(65) Prior Publication Data
US 2022/0378902 A1 Dec. 1, 2022

(30) Foreign Application Priority Data

Aug. 22, 2019 (CN) .......................... 201910777473.5
Aug. 22, 2019 (CN) .......................... 201910777479.2
(Continued)

(51) Int. Cl.
*A61K 39/104* (2006.01)
*A61K 9/00* (2006.01)
(Continued)

(52) U.S. Cl.
CPC .......... *A61K 39/104* (2013.01); *A61K 9/0019* (2013.01); *A61K 9/50* (2013.01);
(Continued)

(58) Field of Classification Search
CPC ................ A61K 41/17; A61K 47/6911; A61K 2039/55555; C12N 13/00
See application file for complete search history.

(56) References Cited

U.S. PATENT DOCUMENTS

2014/0004178 A1* 1/2014 Morici ................. A61K 39/104
424/234.1

FOREIGN PATENT DOCUMENTS

CN 1688334 A 10/2005
WO 2008147816 A2 12/2008
(Continued)

OTHER PUBLICATIONS

Li et al. "X-ray Irradiated Vaccine Confers protection against Pneumonia caused by Pseudomonas Aeruginosa" Feb. 16, 2016, Scientific Reports, vol. 6, Article No. 18823, p. 1-12. (Year: 2016).*
(Continued)

*Primary Examiner* — Daniel E Kolker
*Assistant Examiner* — Amelia Nicole Dickens
(74) *Attorney, Agent, or Firm* — JCIP; Joseph G. Chu

(57) ABSTRACT
The present invention belongs to the field of microbiology, and particularly relates to membrane vesicles (MVs) isolated from bacteria, and an isolation and preparation system and method for the membrane vesicles, and applications of the membrane vesicles. The bacteria of the present invention comprise Gram-positive bacteria and Gram-negative bacteria. The invention uses ionizing irradiation to irradiate bacteria, and isolates and purifies the produced membrane vesicles. The membrane vesicles prepared can be used as a vaccine, a vaccine adjuvant and/or a pharmaceutical carrier. In addition, the present invention provides a biological composition comprising the membrane vesicles and inactivated bacteria. In addition, the present invention also provides a preparation system, and isolation and purification system for bacterial membrane vesicles and the corresponding method. The membrane vesicles obtained by using the
(Continued)

A

B system and method have high yield, high purity and easy to be industrialized.

9 Claims, 4 Drawing Sheets

(30) Foreign Application Priority Data

| | | | |
|---|---|---|---|
| Aug. 22, 2019 | (CN) | .......................... | 201910777595.4 |
| Aug. 22, 2019 | (CN) | .......................... | 201910777606.9 |
| Aug. 22, 2019 | (CN) | .......................... | 201921369450.2 |

(51) Int. Cl.

| | |
|---|---|
| *A61K 9/50* | (2006.01) |
| *A61K 39/00* | (2006.01) |
| *A61K 41/17* | (2020.01) |
| *A61K 47/69* | (2017.01) |
| *A61P 11/00* | (2006.01) |
| *A61P 31/04* | (2006.01) |
| *C12N 1/205* | (2026.01) |

(52) U.S. Cl.

CPC .......... *A61K 41/17* (2020.01); *A61K 47/6911* (2017.08); *A61P 11/00* (2018.01); *A61P 31/04* (2018.01); *C12N 1/205* (2021.05); *A61K 2039/521* (2013.01); *A61K 2039/54* (2013.01); *A61K 2039/55505* (2013.01); *A61K 2039/55555* (2013.01); *A61K 2039/55594* (2013.01)

(56) References Cited

FOREIGN PATENT DOCUMENTS

| | | | | |
|---|---|---|---|---|
| WO | 2012097185 | A2 | 7/2012 | |
| WO | WO-2015144691 | A1 * | 10/2015 | ........... A61K 39/085 |

OTHER PUBLICATIONS

Park et al. Pulmonary Inflammation Induced by Bacteria-Free Outer Membrane Vesicles from Pseudomonas aeruginosa, May 28, 2013, American Journal of Respiratory Cell and Molecular Biology, vol. 49, Issue 4, p. 637-645. (Year: 2013).*

International Search Report for International Application No. PCT/CN2019/106654.

Written Opinion of International Searching Authority for International Application No. PCT/CN2019/106654.

Cai, W. et al. "Bacterial outer membrane vesicles, a potential vaccine candidate in interatcions with host cells based" Diagnostic Pathology, vol. 13, Dec. 31, 2018 (Dec. 31, 2018), Article 95, pp. 1-12.

Gamalier, J.P. et al. "Increased production of outer membrane vesicles by cultured freshwater bacteria in response to ultraviolet radiation" Microbiological Research, vol. 194, Nov. 3, 2016 (Nov. 3, 2016), pp. 38-46.

Yi, Jie et al. "Advances in Outer Membrane Vesicles of Gram-Negative Bacteria as Sub-Unit Vaccines—A Review" Acta Microbiologica Sinica, vol. 56, No. 6, Jan. 11, 2016 (Jan. 11, 2016) Abstract only.

Structures of gram-negative cell walls and their derived membrane vesicles, Beveridge T, Journal of Bacteriology, 1999 vol. 181(16) pp. 4725-4733).

Biological functions and biogenesis of secreted bacterial outer membrane vesicles, Kulp A, Kuehn M, Annual Review of Microbiology, 2010 vol. 64(1) pp. 163-184.

Devos S, Van Oudenhove L, Stremersch S, Van Putte W, De Rycke R, et al. The effect of imipenem and diffusible signaling factors on the secretion of outer membrane vesicles and associated Ax21 proteins in Stenotrophomonas maltophilia [J]. Frontiers in Microbiology, 2015 vol. 6 pp. 298.

Yi, Jie et al. "Advances in Outer Membrane Vesicles of Gram-Negative Bacteria as Sub-Unit Vaccines-A Review" Acta Microbiologica Sinica, vol. 56, No. 6, Jan. 11, 2016 (Jan. 11, 2016).

* cited by examiner

A B

Control

Treatment

CD4⁺ T cell proliferation in interaction with DCs

BACTERIAL MEMBRANE VESICLES, AND SEPARATION AND PREPARATION SYSTEM AND METHOD THEREFOR

PRIORITY APPLICATIONS

The present application claims priority from Chinese invention patent applications 1) 201910777479.2 "BACTERIAL MEMBRANE VESICLE, AND PREPARATION METHOD AND APPLICATION THEREOF", 2) 201910777473.5 "*Staphylococcus aureus* MEMBRANE VESICLE, AND PREPARATION METHOD AND APPLICATION THEREOF", 3) 201910777606.9 "*Pseudomonas aeruginosa* MEMBRANE VESICLE, AND PREPARATION METHOD AND APPLICATION THEREOF", 4) 201921369450.2 "A PRODUCTION SYSTEM, AND ISOLATION AND PURIFICATION SYSTEM FOR BACTERIAL MEMBRANE VESICLE", 5) 201910777595.4 "A PRODUCTION SYSTEM, AND ISOLATION AND PURIFICATION SYSTEM AND METHOD FOR BACTERIAL MEMBRANE VESICLE" filed on Aug. 22, 2019, which are incorporated by reference in their entirety.

TECHNICAL FIELD

The present invention belongs to the field of microbiology, and particularly relates to a bacterial membrane vesicle, an isolation and preparation system and method for the membrane vesicle, and applications of the membrane vesicle.

BACKGROUND

Membrane vesicles (MVs) are vesicle-like products produced from the outer membrane of bacterial cells (including gram-positive bacteria and gram-negative bacteria), which are mostly spherical with a diameter of about 20-250 nm (Structures of gram-negative cell walls and their derived membrane vesicles, Beveridge T, Journal of Bacteriology, 1999 vol: 181(16) pp: 4725-33). Bacterial membrane vesicles contain a variety of biologically active macromolecules such as nucleic acids, lipopolysaccharides and outer membrane proteins as well as metal ions, enzymes, signaling molecules, etc. (Biological functions and biogenesis of secreted bacterial outer membrane vesicles, Kulp A, Kuehn M, Annual Review of Microbiology, 2010 vol: 64(1) pp: 163-184). Bacterial membrane vesicles play an important role in a variety of biological activities of bacteria, such as production of virulence factors, stress response, nutrient intake, and as a carrier for information exchange among bacteria and between bacteria and host cells.

The production of membrane vesicles occurs at any stage of bacterial growth, which is different from cell lysis and apoptosis. Studies show that the production of membrane vesicles can be induced by the conditions such as pressure stimulation, hypoxia and antibiotic stress. However, the yield of naturally occurring bacterial membrane vesicles is low. It is often needed to culture a large amount of bacterial cells to harvest a certain amount of membrane vesicles, and an additional purification process is needed subsequently to obtain membrane vesicles with a certain quality.

Modern technology has the following problems in the production, preparation and purification of bacterial membrane vesicles: 1) although the use of antibiotics, detergents and oxidants can facilitate the production of membrane vesicles, it is also accompanied by toxic residues, which brings uncertainties to applications thereof. 2) The efficiency of producing membrane vesicles by stimulating bacteria with the above intervention factors is relatively low, and the preparation process cannot be conducted in standardized production. 3) The above methods may change the intrinsic conformation and antigenicity of outer membrane of bacteria, thus affecting the vesicles and limiting the subsequent applications thereof.

SUMMARY

In view of the above technical problems, the present invention provides a bacterial membrane vesicle, as well as a system and method for isolating and producing the bacterial membrane vesicle, which comprises five sub-inventions (i.e., A invention, B invention, C invention, D invention and E invention) and various extensions based on the five sub-inventions.

The present invention first discloses membrane vesicles isolated from inactivated bacteria. The inactivated bacteria comprise gram-positive bacteria and gram-negative bacteria, as well as genetically engineered bacteria. The present invention also provides an isolation and preparation method for the membrane vesicles, as well as an application thereof as a vaccine. The present invention first uses ionizing irradiation—X-rays to irradiate bacteria, and isolates and purifies the produced MVs. The prepared MVs can be used as a vaccine, a vaccine adjuvant and/or a pharmaceutical carrier.

In another aspect, the present invention also discloses membrane vesicles isolated from inactivated *Pseudomonas aeruginosa*. The present invention also provides an isolation and preparation method for the membrane vesicles, as well as an application thereof as a vaccine, and an application of the bacterial vaccine. The present invention first uses ionizing irradiation—X-rays to irradiate *Pseudomonas aeruginosa*, and isolates and purifies the produced MVs. The prepared MVs can be used as a vaccine, a vaccine adjuvant and/or a pharmaceutical carrier.

In another aspect, the present invention also discloses membrane vesicles isolated from inactivated *Staphylococcus aureus*. The present invention also provides an isolation and preparation method for the membrane vesicles, as well as an application thereof as a vaccine, and an application of the bacterial vaccine. The present invention first uses ionizing irradiation—X-rays to irradiate *Staphylococcus aureus*, and isolates and purifies the produced MVs. The prepared MVs can be used as a vaccine, a vaccine adjuvant and/or a pharmaceutical carrier.

In another aspect, the present invention also discloses a production system for bacterial membrane vesicles, which is provided with a fermenter, ultraviolet spectrophotometry equipment and irradiation equipment in sequence. Bacteria are proliferated through fermentation in the fermenter, and the content of bacteria in a bacterial solution is controlled by the ultraviolet spectrophotometry equipment to be within a certain limit, and then the bacterial solution is irradiated with ionizing irradiation by the irradiation equipment to facilitate the bacteria to produce a large amount of membrane vesicles. Accordingly, the present invention also provides a purification system for bacterial membrane vesicles and an isolation system for bacterial membrane vesicles. The membrane vesicles prepared by the system have high yield and high purity and are easy to produce in an industrialized process.

In another aspect, the present invention also discloses a production system and method for bacterial membrane vesicles, wherein the production system is provided with a fermenter, ultraviolet spectrophotometry equipment and irradiation equipment in sequence. Bacteria are proliferated through fermentation in the fermenter, and the content of bacteria in a bacterial solution is controlled by the ultraviolet spectrophotometry equipment to be within a certain limit, and then the bacterial solution is irradiated with ionizing irradiation by the irradiation equipment to facilitate the bacteria to produce a large amount of membrane vesicles, thus increasing the content of membrane vesicles. Accordingly, the present invention also provides an isolation and purification system and a purification method for bacterial membrane vesicles; the membrane vesicles prepared by the method have high yield and high purity and are easy to produce in an industrialized process.

The Present Invention has the Following Beneficial Effects:

The present invention first uses ionizing irradiation—X-rays to irradiate bacteria, and isolates and purifies the produced MVs. No antibiotics or other chemical irritant substances are added, so the adverse effects caused by irritant substance residues and the irritant substances themselves on the membrane vesicles are avoided. At the same time, the technical process is simple and suitable for industrial large-scale and standardized production. Due to high vesicle yield, high efficiency, and good amplification and purification effects, it can be used for large-scale preparation of vesicles. Compared with normal vesicles, the prepared vesicles have a yield increased by tens of times and have better immunogenicity. The bacterial membrane vesicles obtained after optimized production have a broad prospect for subsequent further development and application. In addition, the bacterial membrane vesicles prepared by the present invention can be directly used as a vaccine.

The production system for bacterial membrane vesicles provided by the present invention can facilitate the large-scale production of membrane vesicles produced by bacteria, which is suitable for industrialized production. The purification and isolation system for bacterial membrane vesicles provided by the present invention can remove fermentation wastewater, bacterial flagella and bacterial secretions, and the obtained membrane vesicles have high purity.

DESCRIPTION OF DRAWINGS

To make the embodiments of the present invention or the technical solutions in the prior art clearer, the drawings required to be used in the description of the embodiments or the prior art will be briefly introduced below. It is obvious that the drawings described below are some embodiments of the present invention, and that other drawings can be obtained from these drawings for those of ordinary skill in the art without making inventive effort.

DETAILED DESCRIPTION

Figure 1:
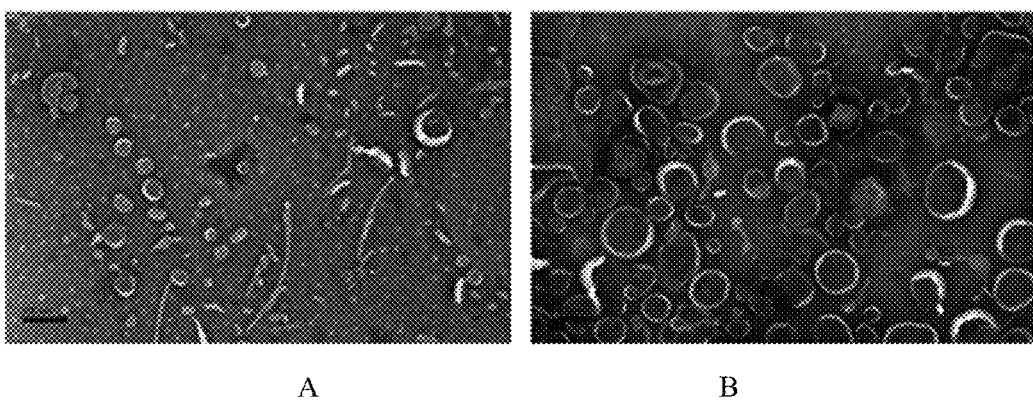
FIG. 1 is a Transmission Electron Microscopy (TEM) image of *Pseudomonas aeruginosa* membrane vesicles (A: membrane vesicles in the control group; B: membrane vesicles in the irradiated group; scale: 200 nm).

To make the objective, the technical solutions and advantages of the embodiments of the present invention clearer, the technical solutions of the embodiments of the present invention will be clearly and completely described below in combination with drawings. It is obvious that the described embodiments are some of the embodiments of the present invention, not all of the embodiments. Based on the embodiments of the present invention, all other embodiments obtained by those of ordinary skill in the art without making inventive effort shall belong to the protection scope of the present invention.

The embodiments are for the purpose of better illustration of the present invention, but the contents of the present invention are not limited to the embodiments. Therefore, non-essential improvements and adjustments of the embodiments made by those skilled in the art according to the above-mentioned contents of the present invention still belong to the protection scope of the present invention.

It should be noted that the sub-inventions of the present invention (A invention, B invention, C invention, D invention and E invention) can be combined to derive other technical solutions, solve more technical problems, and produce more technical effects. Therefore, the description of each sub-invention herein can be mutually confirmed, explained, illustrated, combined, integrated and merged.

However, the description of each sub-invention herein may involve some identical or similar words. If the identical or similar words conflict or contradict in understanding and meaning, then the understanding and meaning of the words in the description of the respective sub-inventions shall prevail.

A Invention: A Bacterial Membrane Vesicle and a Preparation Method and Applications Thereof A invention belongs to the field of microbiology, and particularly relates to preparation, isolation and purification of a bacterial membrane vesicle, and applications of the membrane vesicle.

Modern technology has the following problems in the production, preparation and purification of bacterial membrane vesicles: 1) although the use of antibiotics, detergents and oxidants can facilitate the production of membrane vesicles, it is also accompanied by toxic residues, which brings uncertainties to applications thereof. 2) The efficiency of producing membrane vesicles by stimulating bacteria with the above intervention factors is relatively low, and the preparation process cannot be conducted in standardized production. 3) The above methods may change the intrinsic conformation and antigenicity of outer membrane of bacteria, thus affecting the vesicles and limiting the subsequent applications thereof.

In view of this, A invention provides a method for isolating bacterial MVs and a method for preparing bacterial MVs. No chemical irritant substances are added in the present invention, so no adverse effect is caused by residues. At the same time, the technical process is simple with high vesicle yield, high efficiency and good amplification effect, which can be used for large-scale preparation of vesicles. Compared with normal vesicles, the vesicles prepared have better immunogenicity and have a broad prospect for subsequent further development and application.

The purpose of A invention is to provide a bacterial membrane vesicle.

Biological particles produced by bacteria, wherein the biological particles are membrane vesicles isolated from inactivated bacteria.

Further, the inactivated bacteria comprise gram-positive bacteria, gram-negative bacteria and genetically engineered bacteria.

Further, the gram-positive bacteria comprise *Staphylococcus aureus, Streptococcus, Corynebacterium diphtheriae, Mycobacterium tuberculosis, Clostridium tetani, Bacillus, corynebacterium*, and genetically engineered bacteria of the above bacteria.

Further, the gram-negative bacteria comprise *Pseudomonas aeruginosa, Acinetobacter baumannii, Escherichia coli, Salmonella typhi, Diplococcus meningitidis, Proteusbacillus vulgaris, Shigella*, and genetically engineered bacteria of the above bacteria.

Further, the inactivated bacteria are anaerobic bacteria.

Further, the anaerobic bacteria include *Helicobacter pylori*, Denitrifying bacteria or *Fusobacterium nucleatum*.

A biological composition, containing the above membrane vesicles and the above inactivated bacteria.

Further, the above membrane vesicles are combined with the inactivated bacteria to form a vaccine, and/or as the latter's vaccine adjuvant or pharmaceutical carrier.

The purpose of A invention is also to provide an isolation method for membrane vesicles.

A method for isolating membrane vesicles from bacteria, wherein the bacteria comprise gram-positive bacteria and gram-negative bacteria, and the method specifically comprises the following steps:

1) Isolating bacterial cells in bacterial solution for culture of bacteria from culture medium, and collecting supernatant 1;
2) Centrifuging the supernatant 1 with a high-speed centrifuge, and collecting supernatant 2; and
3) Centrifuging the supernatant 2 with an ultra-high-speed centrifuge to precipitate membrane vesicles.

Further, isolation method in the step 1) comprises centrifugation, column chromatography, or dialysis bag concentration.

Further, the supernatant 2 collected in the step 2) is subjected to dialysis bag concentration prior to the step 3). In some embodiments, the dialysis bag selected can concentrate substances greater than 100 KD.

Further, the membrane vesicles are resuspended with a buffer solution, the buffer solution comprises 50 mM Tris, 5 mM NaCl and 1 mM $MgSO_4$ calculated as a volume unit of 1 L and has a pH of 7.4.

A method for preparing a biological composition, comprising: collecting the bacterial cells isolated in the step 1) in the above isolation method for membrane vesicles, and mixing the bacterial cells with the membrane vesicles obtained in the step 3) to form the biological composition.

Further, in the step 1), the supernatant 1 is filtered with a 0.3-0.5 µM filter to remove impurities.

Preferably, the supernatant 1 is filtered with a 0.45 µM filter to remove impurities.

Further, the isolation method in the step 1) is centrifugation, the centrifugation speed is 100-10000 g, and the centrifugation time is 10-60 min.

Preferably, the centrifugation speed in the step 1) is 400-8000 g, and the centrifugation time is 10-30 min.

Further, the high-speed centrifugation speed in the step 2) is 5000-25000 g, and the high-speed centrifugation time is 10-100 min.

Preferably, the high-speed centrifugation speed in the step 2) is 10000-20000 g, and the high-speed centrifugation time is 30-60 min.

Further, the ultra-high-speed centrifugation speed in the step 3) is 5000-150000 g, and the ultra-high-speed centrifugation time is 60-600 min.

Preferably, the ultra-high-speed centrifugation speed in the step 3) is 15000-150000 g, and the ultra-high-speed centrifugation time is 60-180 min.

Further, the gram-positive bacteria comprise *Staphylococcus aureus, Streptococcus, Corynebacterium diphtheriae, Mycobacterium tuberculosis, Clostridium tetani, Bacillus, corynebacterium*, and genetically engineered bacteria of the above bacteria.

Further, the gram-negative bacteria comprise *Pseudomonas aeruginosa, Acinetobacter baumannii, Escherichia coli, Salmonella typhi, Diplococcus meningitidis, Proteusbacillus vulgaris, Shigella*, and genetically engineered bacteria of the above bacteria.

Further, the bacteria are inactivated bacteria.

Membrane vesicles obtained by the above method.

The purpose of the present invention is also to provide a preparation method.

A method for preparing biological particles, wherein specifically comprising the following steps:

1) Augmentation of membrane vesicles:
   culturing bacteria to logarithmic growth phase; collecting bacterial cells, resuspending the bacterial cells and then irradiating the bacterial cells with ionizing irradiation to obtain irradiated bacteria;
2) Isolation and purification of membrane vesicles:
   Isolating membrane vesicles produced by the irradiated bacteria from the irradiated bacteria to obtain the membrane vesicles using the above method for isolating membrane vesicles.

Further, the ionizing irradiation is X-rays, and the irradiation dose is 500-3000 Gy. The irradiation dose specifically comprises: 500-600 Gy, 600-700 Gy, 700-800 Gy, 800-900 Gy, 900-1000 Gy, 1000-1100 Gy, 1100-1200 Gy, 1200-1300 Gy, 1300-1400 Gy, 1400-1500 Gy, 1500-1600 Gy, 1600-1700 Gy, 1700-1800 Gy, 1800-1900 Gy, 1900-2000 Gy, 2100-2200 Gy, 2200-2300 Gy, 2300-2400 Gy, 2400-2500 Gy, 2500-2600 Gy, 2600-2700 Gy, 2700-2800 Gy, 2800-2900 Gy and 2900-3000 Gy.

Preferably, the irradiation dose is 500-1000 Gy. The irradiation dose specifically comprises: 500-600 Gy, 600-700 Gy, 700-800 Gy, 800-900 Gy and 900-1000 Gy.

Further, $OD_{600}$ value of the bacteria in logarithmic growth phase in the step 1) is 0.3-0.8.

Preferably, the $OD_{600}$ value of the bacteria in logarithmic growth phase in the step 1) is 0.5-0.7.

Further, in the step 1), the bacterial cells are resuspended with phosphate buffer solution or sterile normal saline.

Preferably, in the step 1), the bacterial cells are resuspended with phosphate buffer solution.

Further, in the step 1), the bacterial cells are resuspended to an $OD_{600}$ value of 20-80.

Preferably, in the step 1), the bacterial cells are resuspended to an $OD_{600}$ value of 40-60.

Membrane vesicles obtained by the above method.

The content of nucleic acids and the content of proteins in the membrane vesicles prepared by the above method are increased by 10-20 times, compared with those prepared from bacteria not irradiated with ionizing irradiation.

The purpose of the present invention is also to provide applications of membrane vesicles and inactivated bacteria.

An application of the above membrane vesicles (hereinafter referred to as the membrane vesicles prepared by A invention) as an immunogen.

An application of the membrane vesicles prepared by A invention as an immune response enhancer.

An application of the membrane vesicles prepared by A invention as a vaccine for treating bacterial infectious diseases.

Further, the bacterial infectious diseases comprise pneumonia, urinary tract infection, meningitis, septicemia, and skin or soft tissue infection.

An application of the membrane vesicles prepared by A invention as a vaccine adjuvant.

Further, the vaccine adjuvant non-specifically changes or enhances the antigen-specific immune response of the body.

An application of the membrane vesicles prepared by A invention as an antigen-presenting cell function enhancer.

Further, the antigen-presenting cell comprises dendritic cells, macrophages and B cells.

An application of the membrane vesicles obtained by irradiation, isolation and purification as an enhancer for the maturation of DC cells.

Further, an application of the membrane vesicles as an enhancer for promoting the significant up-regulation of cell surface molecules CD80, CD86 and MHCII molecules of bone marrow-derived dendritic cells.

An application of the membrane vesicles prepared by A invention as a DC cell antigen-presenting ability enhancer.

An application of the membrane vesicles prepared by A invention combined with DC cells in preparation of a proliferation agent for CD4+T cells.

A method for promoting proliferation of CD4+T cells, wherein co-culturing membrane vesicles-stimulated and OVA-antigen-phagocytosed DCs with CFSE-labeled CD4+T lymphocytes in vitro, wherein the membrane vesicles are prepared by irradiation.

An application of the membrane vesicles prepared by A invention in preparation of a veterinary drug.

An application of the inactivated bacteria of A invention as a bacterial vaccine.

Embodiment 1 of A Invention

A invention provides a method for isolating and preparing bacterial membrane vesicles. The method comprises the following steps:

1. Culturing bacteria to logarithmic growth phase, wherein $OD_{600}$ value of the bacteria in logarithmic growth phase is 0.3-0.8, and the $OD_{600}$ value of 0.5-0.8 is preferably selected (fermentation can also be performed here to further enrich bacterial cells); collecting bacterial cells, and resuspending the bacterial cells with an appropriate amount of phosphate buffer solution, wherein the ratio of the amount of the added phosphate buffer solution to the total amount of the bacterial cells is that the $OD_{600}$ value of the amount of the bacteria contained in every 1 ml of solution is 20-80, and the $OD_{600}$ value of 40-60 is preferably selected; after resuspension, irradiating the bacterial cells with ionizing irradiation to obtain irradiated bacteria; preferably, irradiating with X-rays, with an irradiation dose of 500-3000 Gy. The irradiation dose specifically comprises: 500-600 Gy, 600-700 Gy, 700-800 Gy, 800-900 Gy, 900-1000 Gy, 1000-1100 Gy, 1100-1200 Gy, 1200-1300 Gy, 1300-1400 Gy, 1400-1500 Gy, 1500-1600 Gy, 1600-1700 Gy, 1700-1800 Gy, 1800-1900 Gy, 1900-2000 Gy, 2100-2200 Gy, 2200-2300 Gy, 2300-2400 Gy, 2400-2500 Gy, 2500-2600 Gy, 2600-2700 Gy, 2700-2800 Gy, 2800-2900 Gy and 2900-3000 Gy.

2. Collecting bacterial solution, centrifuging the bacterial solution and collecting supernatant, and filtering the supernatant with a 0.3-0.5 µM filter to remove the bacteria; wherein the centrifugation speed is 400-8000 g, and the centrifugation time is 10-30 min.

3. Centrifuging the filtered supernatant with a high-speed centrifuge, collecting supernatant, and removing flagella; wherein the high-speed centrifugation speed is 10000-20000 g, and the high-speed centrifugation time is 30-60 min.

4. Centrifuging the supernatant after removal of the flagella with an ultra-high-speed centrifuge to precipitate membrane vesicles; wherein the ultra-high-speed centrifugation speed is 15000-150000 g, and the ultra-high-speed centrifugation time is 60-180 min.

5. Collecting the membrane vesicles to obtain purified membrane vesicles.

Embodiment 2 of A Invention

Preparation, isolation and purification of membrane vesicles by irradiating *Pseudomonas aeruginosa* PAO1 with ionizing irradiation:

1. Streaking *Pseudomonas aeruginosa* PAO1 recovered from −80° C. onto LB plates, and culturing them in an incubator at 37° C. for 16-18 h.

2. Picking monoclonal colonies from the LB plates, inoculating the monoclonal colonies in 20 mL of LB liquid medium, and culturing them at constant temperature of 37° C. at 250 rpm for 16-18 h.

3. Inoculating overnight bacterial solution into 1 L of LB medium to an initial concentration of 0.05 $OD_{600}$/mL and culturing the bacteria to logarithmic growth phase at 37° C. at 250 rpm, and measuring $OD_{600}$ value of the bacterial solution.

4. Transferring the above bacterial solution of the step 3 to a centrifugal barrel, centrifuging the bacterial solution at 5,000 g for 20 min, collecting the bacterial cells and resuspending the bacterial cells with normal saline, and adjusting the concentration of the bacterial cells to about 50 OD.

5. Placing the above bacterial solution in an irradiator with an irradiation dose of 1000 Gy.

6. Centrifuging the irradiated bacterial solution at 8,000×g for 20 min twice and collecting supernatant; filtering the supernatant with a 0.45 µM filter to remove the bacteria and collecting the supernatant again; at the same time, coating a small amount of the supernatant onto the LB plates and culturing them at 37° C. for 24-72 h to confirm that viable bacteria do not exist.

7. Centrifuging the supernatant of the step 6 with a high-speed centrifuge to remove flagella in the supernatant.

8. Centrifuging the supernatant of the step 7 with an ultra-high-speed centrifuge to precipitate membrane vesicles.

9. Discarding the supernatant, resuspending the precipitate with MV buffer, and storing it at −80° C.

10. Observing the extracted membrane vesicles of the normal group and the membrane vesicles of the experimental group of the present invention by transmission electron microscopy. At the same time, determining the contents of substances in the extracted membrane vesicles of the normal group and the membrane vesicles of the experimental group of the present invention, including determining the content of DNAs, the content of RNAs and the content of proteins therein. Finally, measuring the particle sizes of the extracted membrane vesicles of the normal group and the membrane vesicles of the experimental group of the present invention.

Experimental Results:

According to the results of transmission electron microscopy, the ionizing irradiation can stimulate *Pseudomonas aeruginosa* PAO1 to produce membrane vesicles, and the number of membrane vesicles is larger in the experimental group. No significant difference is found in the form and size of the vesicles compared with those of the normal control group. See FIG. 1.

Figure 2:
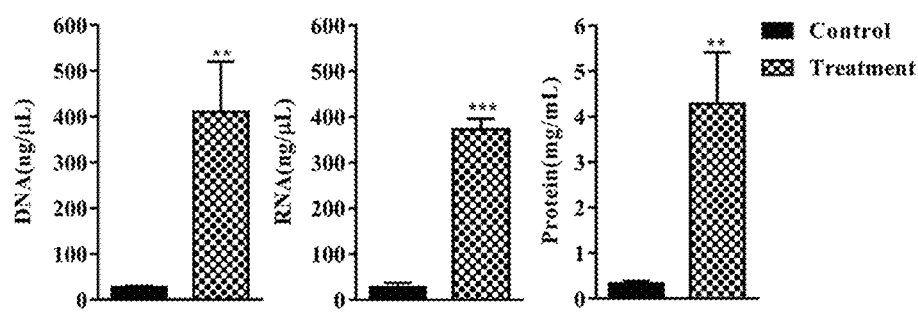
FIG. 2 is a chart for determination of contents of substances in *Pseudomonas aeruginosa* membrane vesicles.

Determination results of contents of substances: the content of nucleic acids and the content of proteins in the membrane vesicles prepared in the experimental group are increased by 10-20 times compared with those in the normal control group. See FIG. 2. See Table 1 for specific measurement data.

TABLE 1

| Determination of contents of substances in membrane vesicles | | | | |
|---|---|---|---|---|
| Irradiation dose Gy | DNA ng/μL | RNA ng/μL | Protein μg/mL | Endotoxin (EU/ml) |
| — | 24.8 | 19.7 | 262.7 | $1.28 \times 10^5$ |
| 980 | 469.0 | 364.0 | 4551.0 | $1.07 \times 10^6$ |

Figure 3:
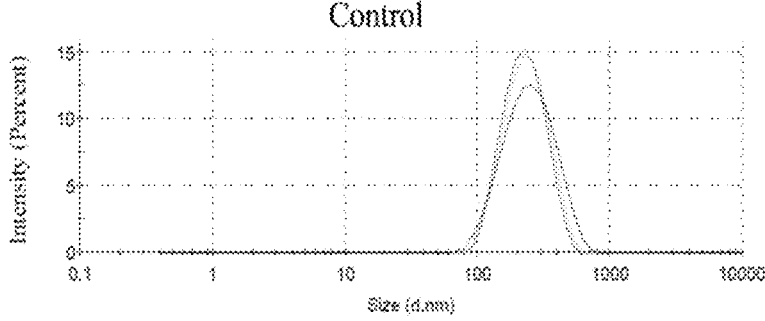
FIG. 3 is a particle size distribution chart of *Pseudomonas aeruginosa* membrane vesicles.
Figure 3:
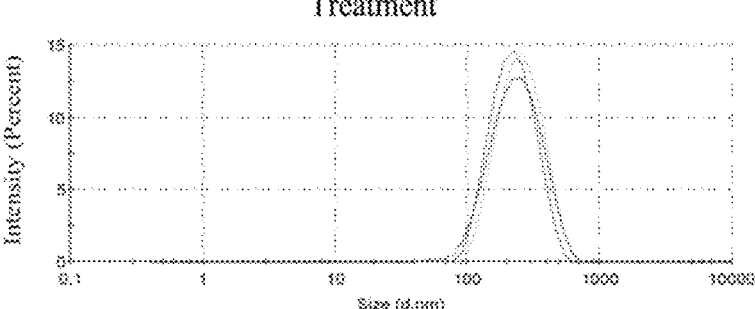

Data of the particle size distribution chart shows that no significant difference is found between the size of the membrane vesicles prepared in the normal control group and that in the experimental group, and the particle size is about 150 nm on average. See FIG. 3. See Table 2 for specific measurement data.

TABLE 2

| Particle size | | |
|---|---|---|
| Irradiation dose Gy | Average particle size (nm) | Peak(nm) |
| — | 152.2 | 192.6 |
| 980 | 146.5 | 222.9 |

3. Embodiment of A Invention

Preparation of membrane vesicles by irradiating *Staphylococcus aureus* ATCC 25923 with ionizing irradiation:

1. Streaking *Staphylococcus aureus* ATCC 25923 recovered from −80° C. onto LB plates, and culturing them in an incubator at 37° C. for 16-18 h.

2. Picking monoclonal colonies from the LB plates, inoculating the monoclonal colonies in 100 mL of LB liquid medium, and culturing the monoclonal colonies at constant temperature of 37° C. at 250 rpm for 16-18 h.

3. Inoculating overnight bacterial solution into 2 L of LB medium to an initial concentration of 0.05 $OD_{600}$/mL, culturing the bacteria to logarithmic growth phase at 37° C. at 250 rpm, and measuring $OD_{600}$ value of the bacterial solution.

4. Transferring the above bacterial solution of 3) to a 2 L centrifugal barrel, centrifuging at 5,000 g for 20 min, collecting the bacterial cells and resuspending the bacterial cells with normal saline, adjusting the concentration of the bacterial cells to about 50 OD, diluting 100 μL of the resuspension 107 times, and then coating the diluted resuspension onto plates to count viable bacteria.

5. Placing the above bacterial solution in an irradiator, with an irradiation dose of 1000 Gy.

6. Centrifuging the irradiated bacterial solution at 8,000×g for 20 min twice, and collecting supernatant; filtering the supernatant with a 0.45 μM filter to remove the bacteria, and collecting the obtained supernatant again; at the same time, coating a small amount of the supernatant onto the LB plates and culturing them at 37° C. for 24-72 h to confirm that viable bacteria do not exist.

7. Centrifuging the supernatant of the step 6 with an ultra-high-speed centrifuge at 39,000×g for 90 min to precipitate MVs.

8. Discarding the supernatant, resuspending the precipitate with 2 mL of MV buffer, and storing at −80° C.

9. Determining the contents of substances in the extracted membrane vesicles of the normal group and the membrane vesicles of the experimental group of the present invention, including determining the content of DNAs, the content of RNAs and the content of proteins therein.

Experimental Results

Figure 4:
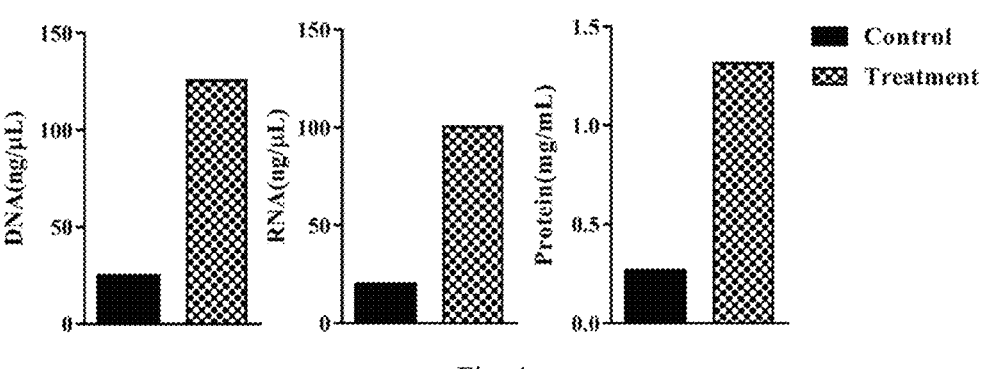
FIG. 4 is a chart for determination of contents of substances in *Staphylococcus aureus* membrane vesicles.

Determination results show that, for *Staphylococcus aureus* ATCC27853, the content of nucleic acids and the content of proteins in the membrane vesicles prepared in the experimental group are significantly increased, indicating that irradiating gram-positive bacteria with ionizing irradiation can also stimulate the production of membrane vesicles. See FIG. 4.

Embodiment 4 of A Invention

Immunomodulatory effects of irradiated bacterial membrane vesicles—promoting maturation of dendritic cells:

Dendritic cells (DCs) are the main antigen-presenting cells of the body, and have the main function of phagocytosing and processing antigen molecules as well as presenting them to T cells. The DCs are the known most powerful and the only professional antigen-presenting cell that can activate resting T cells in the body, and are a key link in initiating, regulating and maintaining immune responses. The maturation of the DCs determines the immune response or immune tolerance of the body. Co-stimulatory molecules B7 (B7-1=CD80 and B7-2=CD86) on the surfaces of the DCs can be bound to CD28 or CD152 molecules on the surfaces of T cells, to enhance or weaken the MHC-TCR signal transduction between DCs and T cells. The main characteristics of mature DCs are changes in the expression of co-stimulatory molecules CD80 and CD86, reduced ability to phagocytose antigens and enhanced the ability to process and present antigens (increased MHCII molecules expression), and interaction with T lymphocytes.

1. Culture and induction of mouse bone marrow-derived dendritic cells (BMDC): taking 6-8 week old C57 female mice, aseptically separating mouse femurs, removing the muscles on the femurs, and cutting both ends of the femurs; rinsing the bone lumens with PBS until the bone lumens turn white; filtering PBS suspension and then centrifuging it at 1200 rpm for 5 min; removing supernatant; and adding 5 ml of red blood cell lysis buffer to resuspend the cells. After standing for 15 min, centrifuging the lysis product at 1200 rpm for 5 min, and removing the supernatant; adding 50 ml of 1640 complete medium (20 ng/ml GM-CSF, 10% FBS and 50 mM of 2-mercaptoethanol) to resuspend the cells. After uniform mixing, dividing the cells into 5 petri dishes and culturing them in an incubator. Changing the medium every 2 days and collecting the cells on the 7th day.

2. BMDC stimulation: taking the BMDC cells induced for 7 days, and repeatedly blowing the cells in a 6-well plate to detach adherent cells; collecting the cell suspension, centrifuging it at 1100 rpm for 5 min, removing supernatant, and adding 1 ml of medium to resuspend the cells, and adjusting the cell concentration to $1\times10^6$/ml after counting viable cells, and inoculating 2 ml of the cells into a new 6-well plate. Each stimulator will be added respectively and uniformly mixed: whole-cell bacteria, whole-cell bacteria+vesicles, and vesicles at a final concentration of 15 μg/mL (based on protein). Continuing to culture them for 24 hours and adding an equal volume of PBS to the growth control group.

3. Maturation markers detection by flow cytometry: after 24 h, taking out the 6-well plate, repeatedly blowing the cells to detach them, collecting the cell suspension into a Flow Cytometry Tube, centrifuging it at 1500 rpm for 3 min, removing supernatant, adding 1 ml of PBS to continue centrifugation at 1500 rpm for 3 min, then removing the supernatant and repeatedly washing for 3 times. Adding CD11c/CD80/CD86/MHCII antibodies and incubating at room temperature for 30 min in the dark; at the same time, setting an isotype control group as the negative control group (adding isotype controls of CD11c/CD80/CD86/MHCII). After incubation, adding PBS to wash twice, then adding 200 μl of PBS to resuspend the cells, and detecting the cells by flow cytometry.

4. Result processing: analyzing the ratio of CD80/CD86/MHICII in CD11c cells by flow cytometry software.

Figure 5:
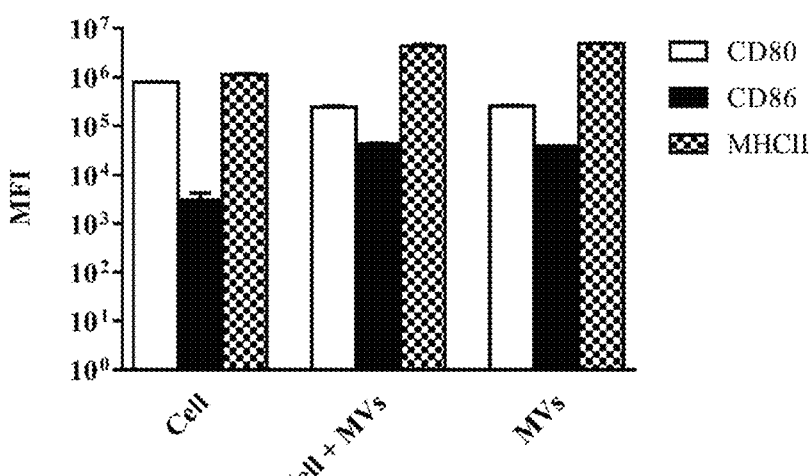
FIG. 5 shows that irradiated membrane vesicles promote significant up-regulation of cell surface molecules CD80, CD86 and MHCII molecules of bone marrow-derived dendritic cells.

Experimental Results:

Compared with the whole-cell bacteria, the vesicles of the experimental group (MVs) treated by X-rays can significantly up-regulate the surface costimulatory molecules CD80, CD86 and MHCII of DCs after stimulation, and these surface molecules are markers of dendritic cell maturation. In conclusion, it is proved that the vesicles can significantly promote the differentiation and maturation of DCs. See FIG. 5.

Embodiment 5 of A Invention

The phagocytic ability of DC cells is detected by detecting the fluorescence intensity of FITC-dextran.

DC cells have strong antigen endocytosis and processing abilities. The DC cells have strong phagocytic ability in an immature state when not in contact with antigen. After in contact with antigen and activated, the DC cells become mature with low phagocytic ability and enhanced antigen-presenting ability. In the experiment, by detecting the fluorescence intensity of the FITC-dextran, the amount of the dextran phagocytosed by DC is determined to detect whether the phagocytic ability of DC is enhanced.

1. Culture and induction of BMDC cells (same as the above).

2. Stimulation: collecting the cells on the 7th day, blowing down all the cells, then centrifuging and resuspending the cells for counting, then inoculating the cells into a 6-well plate with $1\times10^6$ cells per well, and respectively adding the stimulator: adding an equal volume of PBS to the GC group, adding the same concentration of membrane vesicles (by protein level) to the control group and the treatment group and then culturing them at 37° C. for 24 h.

3. Phagocytosis and detection: adding the dextran (5 μg/ml), and after culture for 1 h, aspirating the cells into a Flow Cytometry Tube; washing the cells with PBS for 3 times; adding CD11c antibody and incubating at room temperature for 30 min in the dark; washing the cells with PBS for 3 times; and detecting the fluorescence of FITC by flow cytometry.

4. Result processing: analyzing the ratio of FITC in CD11c cells by flow cytometry software.

Figure 6:
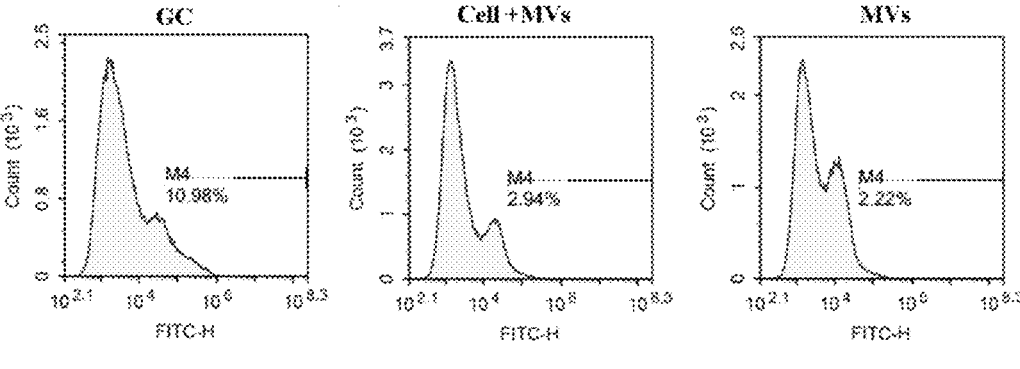
FIG. 6 is a histogram showing the phagocytosis ability of DC cells stimulated by irradiated membrane vesicles.

Experimental Results:

In order to detect the phagocytic function of DCs, the present invention uses FITC-dextran as a model antigen for phagocytosis of DCs and detects the mean fluorescence intensity value of FITC of CD11c+DCs. The experimental result shows that after the DCs are stimulated by membrane vesicles, the mean fluorescence intensity value of FITC is significantly reduced compared with that of the GC group (growth control group). This experimental result proves again that the vesicles can promote the maturation of DCs, thereby reducing their ability to take up antigen. See FIG. 6.

Embodiment 6 of A Invention

Interaction between mature DCs and T cells stimulated by bacterial membrane vesicles in X-ray treatment group:

A. Interaction Between Mature DCs and CD4+T Cells:

The effective cross-antigen presentation of extracellular proteins by DCs plays an important role in the induction of specific cellular immune responses. Therefore, the cross-presentation effect of OVA antigen by DCs stimulated by membrane vesicles is detected. 72 h after co-culture of DCs-T cells, the proliferation of OT-II CD4$^+$T lymphocytes is detected by CFSE flow cytometry. Fluorescent dye CFSE (CFDA-SE), namely carboxyfluorescein diacetate, succinimidyl ester, is a cell staining reagent that can fluorescently label live cells. CFDA-SE can be irreversibly coupled to cellular proteins by binding to intracellular amines after entering cells. In the process of cell division and proliferation, the CFSE-labeled fluorescence can be equally distributed to two daughter cells, and the fluorescence intensity is half that of the parental cells. Therefore, the percentage of cells with weak CFSE fluorescence can be counted by flow cytometry to obtain the proportion of proliferating cells.

1. Culture and induction of BMDC cells (same as the previous embodiment).

2. Antigen phagocytosis: culturing DCs which are cultured for 7 days in a medium containing 10 μg/ml OVA for 24 h to serve as GC (growth control group); adding vesicles to the MVs group, then centrifuging and collecting antigen-phagocytosed DCs; resuspending the DCs in a normal medium; and applying the DCs in a 96-well plate at a density of $2 \times 10^4$ cells/well, with 100 µl per well, and 3 replicate wells per group.

3. T cell extraction: on the second day, isolating and enriching OVA-specific CD4+T lymphocytes from the spleens of OT-II mice by a magnetic negative selection beads kit from Stem Cell Technologies company.

4. Co-culture of DC and T cells: labeling the sorted CD4$^+$T cells with 1 µM CFSE according to the kit instructions. After labeling, washing the cells for 3 times with PBS and adding the cells to the 96-well plate at a density of $10^5$ cells/well to a final culture volume of 200 µl (CD4:DC=5:1).

5. On the 3rd day after co-culture, detecting the proliferation of CD4+T cell population by CFSE decrement by flow cytometry.

Figure 7:
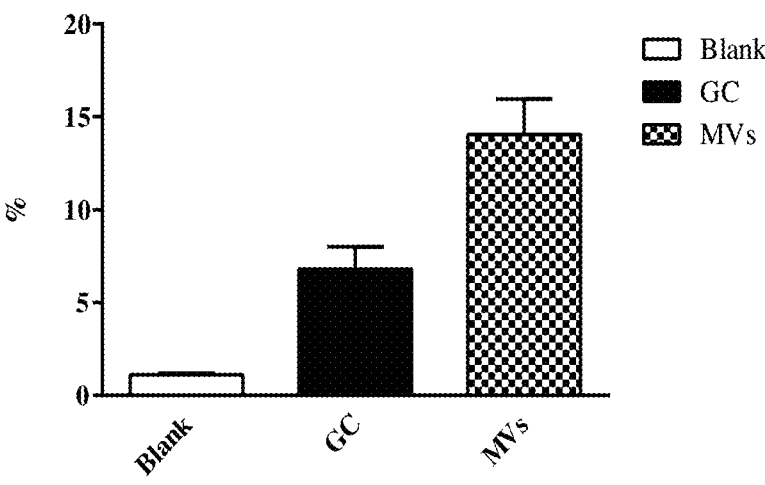
FIG. 7 shows the percentage of proliferation of CD4+T cells after interacting with DC treated with different treatment methods.
Figure 8:
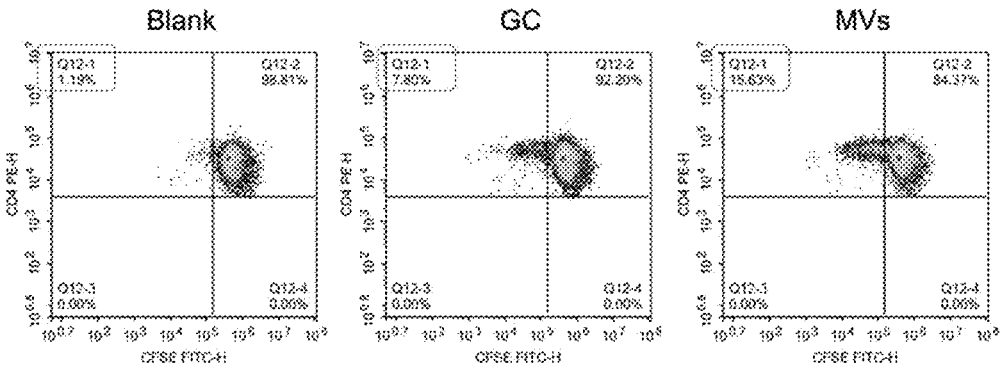
FIG. 8 is a flow cytometry plot of proliferation of CD4+T cells after interacting with DC treated with different treatment methods.

Experimental Results:

Co-culturing membrane vesicles-stimulated and OVA-antigen-phagocytosed DCs with CFSE-labeled OT-II mouse CD4$^+$T lymphocytes in vitro. The analysis results of flow cytometry for CFSE fluorescence intensity show that the proportion of proliferating CD4+T cells is increased. The membrane vesicles (14.05%) can significantly increase the proliferation-promoting effect of OVA-antigen-phagocytosed DCs (6.80%) on specific CD4$^+$T cells. See FIG. 7 and FIG. 8 for details.

B. Promotion of T Cell Proliferation by DCs Treated by the Membrane Vesicles:

The effective cross-antigen presentation of extracellular proteins by DCs plays an important role in the induction of specific cellular immune responses. Therefore, the cross-presentation effect of OVA antigen by DCs stimulated by membrane vesicles is detected. 72 h after co-culture of DCs-T cells, the proliferation of T lymphocytes is detected by CFSE by flow cytometry. Fluorescent dye CFSE (CFDA-SE), namely carboxyfluorescein diacetate, succinimidyl ester, is a cell staining reagent that can fluorescently label live cells. CFDA-SE can be irreversibly coupled to cellular proteins by binding to intracellular amines after entering cells. In the process of cell division and proliferation, the CFSE-labeled fluorescence can be equally distributed to two daughter cells, and the fluorescence intensity is half that of the parental cells. Therefore, the percentage of cells with weak CFSE fluorescence can be counted by flow cytometry to obtain the proportion of proliferating cells.

1. Culture and induction of BMDC cells (same as the previous embodiment).

2. Antigen phagocytosis: culturing DCs which are cultured for 7 days in a medium for 24 h to serve as GC (growth control group); adding vesicles to the MVs group, then centrifuging and collecting antigen-phagocytosed DCs; resuspending the DCs in a normal medium; and applying the DCs in a 96-well plate at a density of $4 \times 10^4$ cells/well, with 100 µl per well, and 3 replicate wells per group.

3. T cell extraction: on the second day, isolating and enriching the T cells of the mice from the spleens of mice one week after one MVs immunization using a magnetic negative selection beads kit from Stem Cell Technologies Company.

4. Co-culture of DC and T cells: labeling the sorted T cells with 1 µM CFSE according to the kit instructions. After labeling, washing the cells for 3 times with PBS and adding the cells to the 96-well plate at a density of $4 \times 10^5$ cells/well to a final culture volume of 200 µl (CD3:DC=10:1).

5. On the 3rd day after co-culture, detecting the proliferation of CD3$^+$, CD8$^+$ and CD4$^+$T cell populations by CFSE decrement by flow cytometry.

Figure 9:
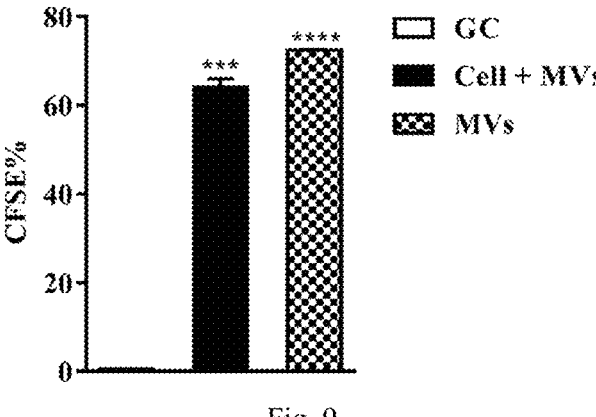
FIG. 9 shows irradiated membrane vesicles enhance the interaction between DC cells and T cells (GC: growth control, dendritic cell growth control group (unstimulated group); Cell+MVs (whole-cell bacteria+membrane vesicle treatment group); MVs (membrane vesicle treatment group)).

Experimental Results:

Co-culturing membrane vesicles-stimulated and OVA-antigen-phagocytosed DCs with CFSE-labeled OT-II mouse CD4$^+$T lymphocytes in vitro. The analysis results of flow cytometry for CFSE fluorescence intensity show that the proportion of proliferating CD4$^+$T cells is increased. As shown in the figure, the fluorescence intensity of the whole-cell bacteria plus vesicle stimulation group is 63.5%, and the fluorescence intensity of the vesicle stimulation group is 71%. It indicates that DCs after vesicle treatment can significantly stimulate the proliferation of CD4$^+$T cells. See FIG. 9.

B Invention: A *Pseudomonas aeruginosa* Membrane Vesicle and a Preparation Method and Applications Thereof B invention belongs to the field of microbiology, and particularly relates to preparation, isolation and purification of a *Pseudomonas aeruginosa* membrane vesicle, and applications of the membrane vesicle.

Modern technology has the following problems in the production, preparation and purification of bacterial membrane vesicles: 1) although the use of antibiotics, detergents and oxidants can facilitate the production of membrane vesicles, it is also accompanied by toxic residues, which brings uncertainties to applications thereof. 2) The efficiency of producing membrane vesicles by stimulating bacteria with the above intervention factors is relatively low, and the preparation process cannot be conducted in standardized production. 3) The above methods may change the intrinstic conformation and antigenicity of outer membrane of bacteria, thus affecting the vesicles and limiting the subsequent applications thereof.

B invention provides a method for isolating *Pseudomonas aeruginosa* MVs and a method for preparing *Pseudomonas aeruginosa* MVs. An international advanced technology is adopted in the present invention, and no chemical irritant substances are added in the present invention, so no adverse effect is caused. At the same time, the technical process is simple with high vesicle yield, high efficiency and good amplification effect, which can be used for large-scale preparation of vesicles. Compared with normal vesicles, the vesicles prepared have better immunogenicity and have a broad prospect for subsequent further development and application.

The purpose of B invention is to provide a *Pseudomonas aeruginosa* vaccine.

A *Pseudomonas aeruginosa* vaccine, wherein the *Pseudomonas aeruginosa* vaccine contains membrane vesicles isolated from inactivated *Pseudomonas aeruginosa*.

A biological composition, containing isolated membrane vesicles and inactivated *Pseudomonas aeruginosa*.

Further, the membrane vesicles are combined with the inactivated *Pseudomonas aeruginosa* to form a vaccine, and/or as the latter's vaccine adjuvant or pharmaceutical carrier.

The purpose of B invention is also to provide an isolation method for *Pseudomonas aeruginosa* membrane vesicles.

A method for isolating membrane vesicles from *Pseudomonas aeruginosa*, comprising the following steps:

1) Culturing bacteria to logarithmic growth phase;
2) Collecting bacterial solution, centrifuging the bacterial solution and collecting supernatant 1, and filtering the supernatant 1 with a 0.3-0.5 µM filter to remove the bacteria;
3) Centrifuging the filtered supernatant 1 with a high-speed centrifuge, collecting supernatant 2, and removing flagella;
4) Centrifuging the supernatant 2 after removal of the flagella with an ultra-high-speed centrifuge to precipitate and obtain membrane vesicles.

Further, the supernatant in the step 2) is filtered with a 0.45 µM filter to remove the bacteria.

Further, the centrifugation speed in the step 2) is 100-10000 g, and the centrifugation time is 10-60 min.

Preferably, the centrifugation speed is 400-8000 g, and the centrifugation time is 10-30 min.

Further, the high-speed centrifugation speed in the step 3) is 5000-25000 g, and the high-speed centrifugation time is 10-100 min.

Preferably, the high-speed centrifugation speed is 10000-20000 g, and the high-speed centrifugation time is 30-60 min.

Further, the ultra-high-speed centrifugation speed in the step 4) is 5000-150000 g, and the ultra-high-speed centrifugation time is 60-600 min.

Preferably, the ultra-high-speed centrifugation speed is 15000-150000 g, and the ultra-high-speed centrifugation time is 60-180 min.

Further, the *Pseudomonas aeruginosa* are inactivated *Pseudomonas aeruginosa*.

*Pseudomonas aeruginosa* membrane vesicles obtained by the above method.

The purpose of B invention is also to provide a preparation method.

A method for preparing the above *Pseudomonas aeruginosa* vaccine, wherein the method comprises the following steps:

1) Culturing bacteria to logarithmic growth phase (fermentation can also be performed here to further enrich bacterial cells);
2) Collecting bacterial cells, resuspending the bacterial cells with an appropriate amount of phosphate buffer solution or sterile normal saline, and irradiating the bacterial cells with ionizing irradiation;
3) Collecting the irradiated bacterial solution, centrifuging the bacterial solution, collecting supernatant 1, and filtering the supernatant 1 with a 0.3-0.5 µM filter to remove the bacteria;
4) Centrifuging the filtered supernatant 1 with a high-speed centrifuge, collecting supernatant 2;
5) Centrifuging the supernatant at an ultra-high speed to precipitate and obtain membrane vesicles.

Further, $OD_{600}$ value of the bacteria in logarithmic growth phase in the step 1) is 0.3-0.8.

Further, the ratio of the amount of the phosphate buffer solution or sterile normal saline added in the step 2) to the total amount of the bacterial cells is that $OD_{600}$ value of the amount of the bacteria contained in every 1 ml of solution is 20-80.

Further, the ionizing irradiation in the step 2) is X-rays, and the irradiation dose is 500-3000 Gy. The irradiation dose specifically comprises: 500-600 Gy, 600-700 Gy, 700-800 Gy, 800-900 Gy, 900-1000 Gy, 1000-1100 Gy, 1100-1200 Gy, 1200-1300 Gy, 1300-1400 Gy, 1400-1500 Gy, 1500-

1600 Gy, 1600-1700 Gy, 1700-1800 Gy, 1800-1900 Gy, 1900-2000 Gy, 2100-2200 Gy, 2200-2300 Gy, 2300-2400 Gy, 2400-2500 Gy, 2500-2600 Gy, 2600-2700 Gy, 2700-2800 Gy, 2800-2900 Gy and 2900-3000 Gy.

Preferably, the irradiation dose is 500-1000 Gy. The irradiation dose specifically comprises: 500-600 Gy, 600-700 Gy, 700-800 Gy, 800-900 Gy and 900-1000 Gy.

Further, the centrifugation speed in the step 3) is 100-10000 g, and the centrifugation time is 10-60 min.

Preferably, the centrifugation speed is 400-8000 g, and the centrifugation time is 10-30 min.

Further, the supernatant in the step 3) is filtered with a 0.45 µM filter to remove the bacteria.

Further, the high-speed centrifugation speed in the step 4) is 5000-25000 g, and the high-speed centrifugation time is 10-100 min.

Preferably, the high-speed centrifugation speed is 10000-20000 g, and the high-speed centrifugation time is 30-60 min.

Further, the ultra-high-speed centrifugation speed in the step 5) is 5000-150000 g, and the ultra-high-speed centrifugation time is 60-600 min.

Preferably, the ultra-high-speed centrifugation speed is 15000-150000 g, and the ultra-high-speed centrifugation time is 60-180 min.

*Pseudomonas aeruginosa* membrane vesicles and a *Pseudomonas aeruginosa* vaccine obtained by the above method.

The content of nucleic acids and the content of proteins in the *Pseudomonas aeruginosa* membrane vesicles are increased by 10-20 times, compared with those prepared from bacteria not irradiated with ionizing irradiation.

A method for increasing contents of substances in *Pseudomonas aeruginosa* membrane vesicles, wherein the substances include nucleic acids and proteins, the method uses irradiation equipment to treat *Pseudomonas aeruginosa* bacterial solution, irradiation of the irradiation equipment is X-rays, and the irradiation dose is 500-1000 Gy.

The purpose of B invention is also to provide applications of the *Pseudomonas aeruginosa* membrane vesicles and the inactivated *Pseudomonas aeruginosa*.

An application of the *Pseudomonas aeruginosa* membrane vesicles prepared by B invention (hereinafter referred to as the *Pseudomonas aeruginosa* membrane vesicles prepared by B invention) in preparation of a vaccine against bacterial infection, wherein the *Pseudomonas aeruginosa* membrane vesicles can be used as a vaccine adjuvant.

Further, the vaccine adjuvant can non-specifically changes or enhances the antigen-specific immune response of the body.

Further, wherein the bacterial infection comprises pneumonia, urinary tract infection, meningitis, septicemia, and skin or soft tissue infection.

Further, the *Pseudomonas aeruginosa* membrane vesicles can also be used as a vaccine carrier.

An application of the *Pseudomonas aeruginosa* membrane vesicles prepared by B invention as an immunogen.

An application of the *Pseudomonas aeruginosa* membrane vesicles prepared by B invention as an antigen-presenting cell function enhancer.

Further, the antigen-presenting cell comprises dendritic cells, macrophages and B cells.

An application of the *Pseudomonas aeruginosa* membrane vesicles prepared by irradiation in preparation of a DC cell growth enhancer, wherein the *Pseudomonas aeruginosa* membrane vesicles can stimulate the significant up-regulation of surface costimulatory molecules CD80, CD86 and MHCII of the DC cells, and promote the maturation and differentiation of the DC cells.

An application of the *Pseudomonas aeruginosa* membrane vesicles prepared by B invention as a DC cell antigen-presenting ability enhancer.

A method for promoting proliferation of CD4+T cells, wherein co-culturing the *Pseudomonas aeruginosa* membrane vesicles-stimulated and OVA-antigen phagocytosing DCs with CFSE-labeled CD4+T lymphocytes in vitro, wherein the *Pseudomonas aeruginosa* membrane vesicles are prepared by irradiation.

An application of the *Pseudomonas aeruginosa* membrane vesicles prepared by B invention in preparation of a veterinary drug.

An application of the *Pseudomonas aeruginosa* membrane vesicles as a bacterial vaccine.

Embodiment 1 of B Invention

B invention provides a system for isolating and preparing *Pseudomonas aeruginosa* membrane vesicles, wherein the system is provided with a fermenter, irradiation equipment, ultraviolet spectrophotometry equipment and centrifugal equipment in sequence; a ray generator of the irradiation equipment is one or more of an X-ray generator, a γ-ray generator and a $Co^{60}$ isotope generator; and the centrifugal equipment includes one or more of a centrifuge, a high-speed centrifuge and an ultra-high-speed centrifuge. See FIG. 10.

Embodiment 2 of B Invention

B invention provides a method for preparing *Pseudomonas aeruginosa* membrane vesicles. The method comprises the following steps:
1) Culturing bacteria to logarithmic growth phase, wherein $OD_{600}$ value of the bacteria in logarithmic growth phase is 0.3-0.8, and the $OD_{600}$ value of 0.5-0.8 is preferably selected (fermentation can also be performed here to further enrich bacterial cells);
2) Collecting bacterial cells, resuspending the bacterial cells with an appropriate amount of phosphate buffer solution or sterile normal saline wherein the ratio of the amount of the added phosphate buffer solution to the total amount of the bacterial cells is that the $OD_{600}$ value of the amount of the bacteria contained in every 1 ml of solution is 20-80, and the $OD_{600}$ value of 40-60 is preferably selected;
3) Irradiating the bacterial cells with X-rays, with an irradiation dose of 500-3000 Gy. The irradiation dose specifically comprises: 500-600 Gy, 600-700 Gy, 700-800 Gy, 800-900 Gy, 900-1000 Gy, 1000-1100 Gy, 1100-1200 Gy, 1200-1300 Gy, 1300-1400 Gy, 1400-1500 Gy, 1500-1600 Gy, 1600-1700 Gy, 1700-1800 Gy, 1800-1900 Gy, 1900-2000 Gy, 2100-2200 Gy, 2200-2300 Gy, 2300-2400 Gy, 2400-2500 Gy, 2500-2600 Gy, 2600-2700 Gy, 2700-2800 Gy, 2800-2900 Gy and 2900-3000 Gy.
4) Centrifuging the irradiated bacterial solution, wherein the centrifugation speed is 100-10,000 g, and the centrifugation time is 10-60 min. Centrifuging supernatant with a high-speed centrifuge, collecting the supernatant, and removing flagella; wherein the centrifugation speed is 5000-25000 g, and centrifugation time is 10-100 min
5) Centrifuging the supernatant after removal of the flagella with an ultra-high-speed centrifuge to precipitate membrane vesicles; wherein the ultra-high-speed centrifugation speed is 5000-150000 g, and the ultra-high-speed centrifugation time is 60-600 min.
6) Collecting the membrane vesicles.

Embodiment 3 of B Invention

B invention provides a method for isolating and purifying *Pseudomonas aeruginosa* membrane vesicles. The method comprises the following steps:
1) Culturing bacteria to logarithmic growth phase;
2) Collecting bacterial solution, centrifuging the bacterial solution and collecting supernatant, and filtering the supernatant with a 0.45 μM filter to remove the bacteria; wherein the centrifugation speed is 400-8000 g, and the centrifugation time is 10-30 min.
3) Centrifuging the filtered supernatant with a high-speed centrifuge, collecting supernatant, and removing flagella; wherein the high-speed centrifugation speed is 10000-20000 g, and the high-speed centrifugation time is 30-60 min.
4) Centrifuging the supernatant after removal of the flagella with an ultra-high-speed centrifuge to precipitate membrane vesicles; wherein the ultra-high-speed centrifugation speed is 15000-150000 g, and the ultra-high-speed centrifugation time is 60-180 min.
5) Collecting the membrane vesicles.

Embodiment 4 of B Invention

Preparation, isolation and purification of membrane vesicles by irradiating *Pseudomonas aeruginosa* PAO1 with ionizing irradiation:
1. Streaking *Pseudomonas aeruginosa* PAO1 recovered from −80° C. onto LB plates, and culturing them in an incubator at 37° C. for 16-18 h.
2. Picking monoclonal colonies from the LB plates, inoculating the monoclonal colonies in 20 mL of LB liquid medium, and culturing them at constant temperature of 37° C. at 250 rpm for 16-18 h.
3. Inoculating overnight bacterial solution into 1 L of LB medium to an initial concentration of 0.05 $OD_{600}$/mL and culturing the bacteria to logarithmic growth phase at 37° C. at 250 rpm, and measuring $OD_{600}$ value of the bacterial solution.
4. Transferring the above bacterial solution of the step 3 to a centrifugal barrel, centrifuging the bacterial solution at 5,000 g for 20 min, collecting the bacterial cells and resuspending the bacterial cells with normal saline, and adjusting the concentration of the bacterial cells to about 50 OD.
5. Placing the above bacterial solution in an irradiator with an irradiation dose of 1000 Gy.
6. Centrifuging the irradiated bacterial solution at 8,000×g for 20 min twice and collecting supernatant; filtering the supernatant with a 0.45 μM filter to remove the bacteria and collecting the supernatant again; at the same time, coating a small amount of the supernatant onto the LB plates and culturing them at 37° C. for 24-72 h to confirm that viable bacteria do not exist.
7. Centrifuging the supernatant of the step 6 with a high-speed centrifuge to remove flagella in the supernatant.
8. Centrifuging the supernatant of the step 7 with an ultra-high-speed centrifuge to precipitate membrane vesicles.

9. Discarding the supernatant, resuspending the precipitate with MV buffer, and storing it at −80° C.

10. Observing the extracted membrane vesicles of the normal group and the membrane vesicles of the experimental group of the present invention by transmission electron microscopy. At the same time, determining the contents of substances in the extracted membrane vesicles of the normal group and the membrane vesicles of the experimental group of the present invention, including determining the content of DNAs, the content of RNAs and the content of proteins therein. Finally, measuring the particle sizes of the extracted membrane vesicles of the normal group and the membrane vesicles of the experimental group of the present invention.

Experimental Results:

According to the results of transmission electron microscopy, the ionizing irradiation can stimulate *Pseudomonas aeruginosa* PAO1 to produce membrane vesicles, and the number of membrane vesicles is larger in the experimental group. No significant difference is found in the form and size of the vesicles compared with those of the normal control group. See FIG. 1.

Determination results of contents of substances: the content of nucleic acids and the content of proteins in the membrane vesicles prepared in the experimental group are increased by 10-20 times compared with those in the normal control group. See FIG. 2. See Table 1 for specific measurement data.

Embodiment 5 of B Invention

Immunomodulatory effects of irradiated bacterial membrane vesicles—promoting maturation of dendritic cells:

1. Culture and induction of mouse bone marrow-derived dendritic cells (BMDC): taking 6-8 week old C57 female mice, aseptically separating mouse femurs, removing the muscles on the femurs, and cutting both ends of the femurs; rinsing the bone lumens with PBS until the bone lumens turn white; filtering PBS suspension and then centrifuging it at 1200 rpm for 5 min; removing supernatant; and adding 5 ml of red blood cell lysis buffer to resuspend the cells. After standing for 15 min, centrifuging the lysis product at 1200 rpm for 5 min, and removing the supernatant; adding 50 ml of 1640 complete medium (20 ng/ml GM-CSF, 10% FBS and 50 mM of 2-mercaptoethanol) to resuspend the cells. After uniform mixing, dividing the cells into 5 petri dishes and culturing them in an incubator. Changing the medium every 2 days and collecting the cells on the 7th day.

2. BMDC stimulation: taking the BMDC cells induced for 7 days, and repeatedly blowing the cells in a 6-well plate to detach adherent cells; collecting the cell suspension, centrifuging it at 1100 rpm for 5 min, removing supernatant, and adding 1 ml of medium to resuspend the cells, and adjusting the cell concentration to $1 \times 106$/ml after counting viable cells, and inoculating 2 ml of the cells into a new 6-well plate. Each stimulator will be added respectively and uniformly mixed: whole-cell bacteria, whole-cell bacteria+vesicles, and vesicles at a final concentration of 15 µg/mL (based on protein). Continuing to culture them for 24 hours and adding an equal volume of PBS to the growth control group.

3. Maturation markers detection by flow cytometry: after 24 h, taking out the 6-well plate, repeatedly blowing the cells to detach them, collecting the cell suspension into a Flow Cytometry Tube, centrifuging it at 1500 rpm for 3 min, removing supernatant, adding 1 ml of PBS to continue centrifugation at 1500 rpm for 3 min, then removing the supernatant and repeatedly washing for 3 times. Adding CD11c/CD80/CD86/MHCII antibodies and incubating at room temperature for 30 min in the dark; at the same time, setting an isotype control group as the negative control group (adding isotype controls of CD11c/CD80/CD86/MHCII). After incubation, adding PBS to wash twice, then adding 200 µl of PBS to resuspend the cells, and detecting the cells by flow cytometry.

4. Result processing: analyzing the ratio of CD80/CD86/MICII in CD11c cells by flow cytometry software.

Experimental Results:

Compared with the whole-cell bacteria, the vesicles of the experimental group (MVs) treated by X-rays can significantly up-regulate the surface costimulatory molecules CD80, CD86 and MHCII of DCs after stimulation, and these surface molecules are markers of dendritic cell maturation. In conclusion, it is proved that the vesicles can significantly promote the differentiation and maturation of DCs. See FIG. 5.

Embodiment 6 of B Invention

The phagocytic ability of DC cells is detected by detecting the fluorescence intensity of FITC-dextran.

1. Culture and induction of BMDC cells.

2. Stimulation: collecting the cells on the 7th day, blowing down all the cells, then centrifuging and resuspending the cells for counting, then inoculating the cells into a 6-well plate with $1 \times 10^6$ cells per well, and respectively adding the stimulator: adding an equal volume of PBS to the GC group, adding the same concentration of membrane vesicles (by protein level) to the control group and the treatment group and then culturing them at 37° C. for 24 h.

3. Phagocytosis and detection: adding the dextran (5 µg/ml), and after culture for 1 h, aspirating the cells into a Flow Cytometry Tube; washing the cells with PBS for 3 times; adding CD11c antibody and incubating at room temperature for 30 min in the dark; washing the cells with PBS for 3 times; and detecting the fluorescence of FITC by flow cytometry.

4. Result processing: analyzing the ratio of FITC in CD11c cells by flow cytometry software.

Experimental Results:

In order to detect the phagocytic function of DCs, the present invention uses FITC-dextran as a model antigen for phagocytosis of DCs and detects the mean fluorescence intensity value of FITC of CD11c+DCs. The experimental result shows that after the DCs are stimulated by membrane vesicles, the mean fluorescence intensity value of FITC is significantly reduced compared with that of the GC group (growth control group). This experimental result proves again that the vesicles can promote the maturation of DCs, thereby reducing their ability to take up antigen. See FIG. 6.

Embodiment 7 of B Invention

Interaction between mature DCs and T cells stimulated by bacterial membrane vesicles in X-ray treatment group:

A. Interaction Between Mature DCs and CD4+T Cells:

1. Culture and induction of BMDC cells.

2. Antigen phagocytosis: culturing DCs which are cultured for 7 days in a medium containing 10 µg/ml OVA for 24 h to serve as GC (growth control group); adding vesicles to the MVs group, then centrifuging and collecting antigen-phagocytosed DCs; resuspending the DCs in a normal medium; and applying the DCs in a 96-well plate at a density of $2 \times 10^4$ cells/well, with 100 μl per well, and 3 replicate wells per group.

3. T cell extraction: on the second day, isolating and enriching OVA-specific CD4+T lymphocytes from the spleens of OT-II mice by a magnetic negative selection beads kit from Stem Cell Technologies Company.

4. Co-culture of DC and T cells: labeling the sorted CD4$^+$T cells with 1 μM CFSE according to the kit instructions. After labeling, washing the cells for 3 times with PBS and adding the cells to the 96-well plate at a density of $10^5$ cells/well to a final culture volume of 200 μl (CD4:DC=5:1).

5. On the 3rd day after co-culture, detecting the proliferation of CD4+T cell population by CFSE decrement by flow cytometry.

Experimental Results:

Co-culturing membrane vesicles-stimulated and OVA-antigen-phagocytosed DCs with CFSE-labeled OT-II mouse CD4$^+$T lymphocytes in vitro. The analysis results of flow cytometry for CFSE fluorescence intensity show that the proportion of proliferating CD4+T cells is increased. The membrane vesicles (14.05%) can significantly increase the proliferation-promoting effect of OVA-antigen-phagocytosed DCs (6.80%) on specific CD4$^+$T cells. See FIG. 7 and FIG. 8 for details.

B. Promotion of T Cell Proliferation by DCs Treated by the Membrane Vesicles:

1. Culture and induction of BMDC cells.

2. Antigen phagocytosis: culturing DCs which are cultured for 7 days in a medium for 24 h to serve as GC (growth control group); adding vesicles to the MVs group, then centrifuging and collecting antigen-phagocytosed DCs; resuspending the DCs in a normal medium; and applying the DCs in a 96-well plate at a density of $4 \times 10^4$ cells/well, with 100 μl per well, and 3 replicate wells per group.

3. T cell extraction: on the second day, isolating and enriching the T cells of the mice from the spleens of mice one week after one MVs immunization using a magnetic negative selection beads kit from Stem Cell Technologies company.

4. Co-culture of DC and T cells: labeling the sorted T cells with 1 μM CFSE according to the kit instructions. After labeling, washing the cells for 3 times with PBS and adding the cells to the 96-well plate at a density of $4 \times 10^5$ cells/well to a final culture volume of 200 μl (CD3:DC=10:1).

5. On the 3rd day after co-culture, detecting the proliferation of CD3$^+$, CD8$^+$ and CD4$^+$T cell populations by CFSE decrement by flow cytometry.

Experimental Results:

Co-culturing membrane vesicles-stimulated and OVA-antigen-phagocytosed DCs with CFSE-labeled OT-II mouse CD4$^+$T lymphocytes in vitro. The analysis results of flow cytometry for CFSE fluorescence intensity show that the proportion of proliferating CD4$^+$T cells is increased. As shown in the figure, the fluorescence intensity of the whole-cell bacteria plus vesicle stimulation group is 63.5%, and the fluorescence intensity of the vesicle stimulation group is 71%. It indicates that DCs after vesicle treatment can significantly stimulate the proliferation of CD4$^+$T cells. See FIG. 9.

C Invention: A *Staphylococcus aureus* Membrane Vesicle and a Preparation Method and Applications Thereof C invention belongs to the field of microbiology, and particularly relates to preparation, isolation and purification of a *Staphylococcus aureus* membrane vesicle, and applications of the membrane vesicle.

Modern technology has the following problems in the production, preparation and purification of bacterial membrane vesicles: 1) although the use of antibiotics, detergents and oxidants can facilitate the production of membrane vesicles, it is also accompanied by toxic residues, which brings uncertainties to applications thereof. 2) The efficiency of producing membrane vesicles by stimulating bacteria with the above intervention factors is relatively low, and the preparation process cannot be conducted in standardized production. 3) The above methods may change the intrinsic conformation and antigenicity of outer membrane of bacteria, thus affecting the vesicles and limiting the subsequent applications thereof.

C invention provides a method for isolating *Staphylococcus aureus* MVs and a method for preparing *Staphylococcus aureus* MVs. An international advanced technology is adopted in the present invention, and no chemical irritant substances are added in the present invention, so no adverse effect is caused. At the same time, the technical process is simple with high vesicle yield, high efficiency and good amplification effect, which can be used for large-scale preparation of vesicles. Compared with normal vesicles, the vesicles prepared have better immunogenicity and have a broad prospect for subsequent further development and application.

The purpose of C invention is to provide a *Staphylococcus aureus* membrane vesicle.

Biological particles produced by *Staphylococcus aureus*, wherein the biological particles are membrane vesicles isolated from inactivated *Staphylococcus aureus*.

Inactivated *Staphylococcus aureus* containing the above biological particles.

Further, the inactivated *Staphylococcus aureus* are combined with the biological particles which serve as a vaccine, and/or vaccine adjuvant and/or pharmaceutical carrier.

The purpose of C invention is also to provide an isolation method for *Staphylococcus aureus* membrane vesicles.

A method for isolating membrane vesicles from *Staphylococcus aureus*, comprising the following steps:

1) Culturing bacteria to logarithmic growth phase;

2) Collecting bacterial solution, centrifuging the bacterial solution and collecting supernatant 1, and filtering the supernatant 1 with a 0.3-0.5 μM filter to remove the bacteria;

3) Centrifuging the filtered supernatant 1 with a high-speed centrifuge, collecting supernatant 2;

4) Centrifuging the supernatant 2 after removal of the flagella with an ultra-high-speed centrifuge to precipitate and obtain membrane vesicles.

Further, the supernatant in the step 2) is filtered with a 0.45 μM filter to remove the bacteria.

Further, the centrifugation speed in the step 2) is 100-10000 g, and the centrifugation time is 10-60 min.

Preferably, the centrifugation speed is 400-8000 g, and the centrifugation time is 10-30 min.

Further, the high-speed centrifugation speed in the step 3) is 5000-25000 g, and the high-speed centrifugation time is 10-100 min.

Preferably, the high-speed centrifugation speed is 10000-20000 g, and the high-speed centrifugation time is 30-60 min.

Further, the ultra-high-speed centrifugation speed in the step 4) is 5000-150000 g, and the ultra-high-speed centrifugation time is 60-600 min.

Preferably, the ultra-high-speed centrifugation speed is 15000-150000 g, and the ultra-high-speed centrifugation time is 60-180 min.

Further, the *Staphylococcus aureus* are inactivated *Staphylococcus aureus*.

*Staphylococcus aureus* membrane vesicles obtained by the above isolation method.

The purpose of C invention is also to provide a preparation method.

A method for preparing the above biological particles, wherein the method comprises the following steps:

1) Culturing bacteria to logarithmic growth phase;
2) Collecting bacterial cells, resuspending the bacterial cells with an appropriate amount of phosphate buffer solution or sterile normal saline, and irradiating the bacterial cells with ionizing irradiation;
3) Collecting the irradiated bacterial solution, centrifuging the bacterial solution, collecting supernatant 1, and filtering the supernatant 1 with a 0.3-0.5 µM filter to remove the bacteria;
4) Centrifuging the filtered supernatant 1 with a high-speed centrifuge, collecting supernatant 2;
5) Centrifuging the supernatant 2 at an ultra-high speed to precipitate and obtain membrane vesicles.

Further, $OD_{600}$ value of the bacteria in logarithmic growth phase in the step 1) is 0.3-0.8.

Further, the ratio of the amount of the phosphate buffer solution or sterile normal saline added in the step 2) to the total amount of the bacterial cells is that $OD_{600}$ value of the amount of the bacteria contained in every 1 ml of solution is 20-80.

Further, the ionizing irradiation in the step 2) is X-rays, and the irradiation dose is 500-3000 Gy. The irradiation dose specifically comprises: 500-600 Gy, 600-700 Gy, 700-800 Gy, 800-900 Gy, 900-1000 Gy, 1000-1100 Gy, 1100-1200 Gy, 1200-1300 Gy, 1300-1400 Gy, 1400-1500 Gy, 1500-1600 Gy, 1600-1700 Gy, 1700-1800 Gy, 1800-1900 Gy, 1900-2000 Gy, 2100-2200 Gy, 2200-2300 Gy, 2300-2400 Gy, 2400-2500 Gy, 2500-2600 Gy, 2600-2700 Gy, 2700-2800 Gy, 2800-2900 Gy and 2900-3000 Gy.

Preferably, the irradiation dose is 500-1000 Gy. The irradiation dose specifically comprises: 500-600 Gy, 600-700 Gy, 700-800 Gy, 800-900 Gy and 900-1000 Gy.

Further, the centrifugation speed in the step 3) is 100-10000 g, and the centrifugation time is 10-60 min.

Preferably, the centrifugation speed is 400-8000 g, and the centrifugation time is 10-30 min.

Further, the supernatant in the step 3) is filtered with a 0.45 µM filter to remove the bacteria.

Further, the high-speed centrifugation speed in the step 4) is 5000-25000 g, and the high-speed centrifugation time is 10-100 min.

Preferably, the high-speed centrifugation speed is 10000-20000 g, and the high-speed centrifugation time is 30-60 min.

Further, the ultra-high-speed centrifugation speed in the step 5) is 5000-150000 g, and the ultra-high-speed centrifugation time is 60-600 min.

Preferably, the ultra-high-speed centrifugation speed is 15000-150000 g, and the ultra-high-speed centrifugation time is 60-180 min.

*Staphylococcus aureus* membrane vesicles obtained by the above method.

A method for increasing contents of substances in *Staphylococcus aureus* membrane vesicles, wherein the substances include nucleic acids and proteins, the method uses irradiation equipment to treat *Staphylococcus aureus* bacterial solution, irradiation of the irradiation equipment is X-rays, and the irradiation dose is 500-1000 Gy.

The purpose of C invention is also to provide applications of the *Staphylococcus aureus* membrane vesicles and inactivated *Staphylococcus aureus*.

An application of the *Staphylococcus aureus* membrane vesicles prepared by C invention (hereinafter referred to as the *Staphylococcus aureus* membrane vesicles prepared by C invention) in preparation of a vaccine against bacterial infection, wherein the *Staphylococcus aureus* membrane vesicles can be used as a vaccine adjuvant.

Further, the vaccine adjuvant can non-specifically changes or enhances the antigen-specific immune response of the body.

Further, wherein the bacterial infection comprises pneumonia, urinary tract infection, meningitis, septicemia, and skin or soft tissue infection.

Further, the *Staphylococcus aureus* membrane vesicles can also be used as a vaccine carrier.

An application of the *Staphylococcus aureus* membrane vesicles prepared by C invention as an immunogen.

An application of the *Staphylococcus aureus* membrane vesicles prepared by C invention as an antigen-presenting cell function enhancer.

Further, the antigen-presenting cell comprises dendritic cells, macrophages and B cells.

An application of the *Staphylococcus aureus* membrane vesicles prepared by irradiation in preparation of a DC cell growth enhancer, wherein the *Staphylococcus aureus* membrane vesicles can stimulate the significant up-regulation of surface costimulatory molecules CD80, CD86 and MHCII of the DC cells, and promote the maturation and differentiation of the DC cells.

An application of the *Staphylococcus aureus* membrane vesicles prepared by C invention as a DC cell antigen-presenting ability enhancer.

A composition for promoting proliferation of CD4+T cells, wherein the composition comprises the above *Staphylococcus aureus* membrane vesicles and DC cells.

A method for promoting proliferation of CD4+T cells, wherein co-culturing the *Staphylococcus aureus* membrane vesicles-stimulated and OVA-antigen phagocytosing DCs with CFSE-labeled CD4+T lymphocytes in vitro, wherein the *Staphylococcus aureus* membrane vesicles are prepared by irradiation.

An application of the *Staphylococcus aureus* membrane vesicles prepared by C invention in preparation of a veterinary drug.

An application of the *Staphylococcus aureus* membrane vesicles as a bacterial vaccine.

Embodiment 1 of C Invention

C invention provides a system for isolating and preparing *Staphylococcus aureus* membrane vesicles, wherein the system is provided with a fermenter, irradiation equipment, ultraviolet spectrophotometry equipment and centrifugal equipment in sequence; a ray generator of the irradiation equipment is one or more of an X-ray generator, a γ-ray generator and a $Co^{60}$ isotope generator; and the centrifugal equipment includes one or more of a centrifuge, a high-speed centrifuge and an ultra-high-speed centrifuge. See FIG. 10.

Embodiment 2 of C Invention

C invention provides a method for preparing *Staphylococcus aureus* membrane vesicles. The method comprises the following steps:

1) Culturing bacteria to logarithmic growth phase, wherein $OD_{600}$ value of the bacteria in logarithmic growth phase is 0.3-0.8 (fermentation can also be performed here to further enrich bacterial cells);

2) Collecting bacterial cells, resuspending the bacterial cells with an appropriate amount of phosphate buffer solution or sterile normal saline wherein the ratio of the amount of the added phosphate buffer solution to the total amount of the bacterial cells is that the $OD_{600}$ value of the amount of the bacteria contained in every 1 ml of solution is 20-80;

3) Irradiating the bacterial cells with X-rays, with an irradiation dose of 500-3000 Gy. The irradiation dose specifically comprises: 500-600 Gy, 600-700 Gy, 700-800 Gy, 800-900 Gy, 900-1000 Gy, 1000-1100 Gy, 1100-1200 Gy, 1200-1300 Gy, 1300-1400 Gy, 1400-1500 Gy, 1500-1600 Gy, 1600-1700 Gy, 1700-1800 Gy, 1800-1900 Gy, 1900-2000 Gy, 2100-2200 Gy, 2200-2300 Gy, 2300-2400 Gy, 2400-2500 Gy, 2500-2600 Gy, 2600-2700 Gy, 2700-2800 Gy, 2800-2900 Gy and 2900-3000 Gy.

4) Centrifuging the irradiated bacterial solution, wherein the centrifugation speed is 100-10000 g, and the centrifugation time is 10-60 min. Centrifuging supernatant with a high-speed centrifuge, collecting the supernatant, wherein the centrifugation speed is 5000-25000 g, and the centrifugation time is 10-100 min.

5) Centrifuging the supernatant with an ultra-high-speed centrifuge to precipitate membrane vesicles; wherein the ultra-high-speed centrifugation speed is 5000-150000 g, and the ultra-high-speed centrifugation time is 60-600 min.

6) Collecting the membrane vesicles.

Embodiment 3 of C Invention

C invention provides a method for isolating *Staphylococcus aureus* membrane vesicles. The method comprises the following steps:

1) Culturing bacteria to logarithmic growth phase and performing fermentation;

2) Collecting bacterial solution, centrifuging the bacterial solution and collecting supernatant, and filtering the supernatant with a with a 0.3-0.5 μM filter to remove the bacteria; wherein the centrifugation speed is 400-8000 g, and the centrifugation time is 10-30 min.

3) Centrifuging the filtered supernatant with a high-speed centrifuge, collecting supernatant; wherein the high-speed centrifugation speed is 10000-20000 g, and the high-speed centrifugation time is 30-60 min.

4) Centrifuging the supernatant with an ultra-high-speed centrifuge to precipitate membrane vesicles; wherein the ultra-high-speed centrifugation speed is 15000-150000 g, and the ultra-high-speed centrifugation time is 60-180 min.

5) Collecting the membrane vesicles.

Embodiment 4 of C Invention

Preparation of membrane vesicles by irradiating *Staphylococcus aureus* ATCC 25923 with ionizing irradiation:

1. Streaking *Staphylococcus aureus* ATCC 25923 recovered from −80° C. onto LB plates, and culturing them in an incubator at 37° C. for 16-18 h.

2. Picking monoclonal colonies from the LB plates, inoculating the monoclonal colonies in 100 mL of LB liquid medium, and culturing them at constant temperature of 37° C. at 250 rpm for 16-18 h.

3. Inoculating overnight bacterial solution into 2 L of LB medium to an initial concentration of 0.05 $OD_{600}$/mL and culturing the bacteria to logarithmic growth phase at 37° C. at 250 rpm, and measuring $OD_{600}$ value of the bacterial solution.

4. Transferring the above bacterial solution of the step 3 to a 2 L centrifugal barrel, centrifuging the bacterial solution at 5,000 g for 20 min, collecting the bacterial cells and resuspending the bacterial cells with normal saline, and adjusting the concentration of the bacterial cells to about 50 OD. Diluting 100 μL of the resuspended solution to 107 times and coating onto plates to count viable bacteria.

5. Placing the above bacterial solution in an irradiator with an irradiation dose of 1000 Gy.

6. Centrifuging the irradiated bacterial solution at 8,000×g for 20 min twice and collecting supernatant; filtering the supernatant with a 0.45 μM filter to remove the bacteria and collecting the supernatant again; at the same time, coating a small amount of the supernatant onto the LB plates and culturing them at 37° C. for 24-72 h to confirm that viable bacteria do not exist.

7. Centrifuging the supernatant of the step 6 with a ultra-high-speed centrifuge at 39,000×g for 90 min to precipitate MVs.

8. Discarding the supernatant, resuspending the precipitate with 2 mL MV buffer, and storing it at −80° C.

9. Determining the contents of substances in the extracted membrane vesicles of the normal group and the membrane vesicles of the experimental group of the present invention, including determining the content of DNAs, the content of RNAs and the content of proteins therein.

Experimental Results:

Determination results show that, for *Staphylococcus aureus* ATCC27853, the content of nucleic acids and the content of proteins in the membrane vesicles prepared in the experimental group are significantly increased, indicating that ionizing irradiation of gram-positive bacteria can also stimulate the production of membrane vesicles. See FIG. 4.

Embodiment 5 of C Invention

Immunomodulatory effects of irradiated bacterial membrane vesicles—promoting maturation of dendritic cells:

1. Culture and induction of mouse bone marrow-derived dendritic cells (BMDC): taking 6-8 week old C57 female mice, aseptically separating mouse femurs, removing the muscles on the femurs, and cutting both ends of the femurs; rinsing the bone lumens with PBS until the bone lumens turn white; filtering PBS suspension and then centrifuging it at 1200 rpm for 5 min; removing supernatant; and adding 5 ml of red blood cell lysis buffer to resuspend the cells. After standing for 15 min, centrifuging the lysis product at 1200 rpm for 5 min, and removing the supernatant; adding 50 ml of 1640 complete medium (20 ng/ml GM-CSF, 10%

FBS and 50 mM of 2-mercaptoethanol) to resuspend the cells. After uniform mixing, dividing the cells into 5 petri dishes and culturing them in an incubator. Changing the medium every 2 days and collecting the cells on the 7th day.

2. BMDC stimulation: taking the BMDC cells induced for 7 days, and repeatedly blowing the cells in a 6-well plate to detach adherent cells; collecting the cell suspension, centrifuging it at 1100 rpm for 5 min, removing supernatant, and adding 1 ml of medium to resuspend the cells, and adjusting the cell concentration to $1 \times 10^6$/ml after counting viable cells, and inoculating 2 ml of the cells into a new 6-well plate. Each stimulator will be added respectively and uniformly mixed: whole-cell bacteria, whole-cell bacteria+vesicles, and vesicles at a final concentration of 15 μg/mL (based on protein). Continuing to culture them for 24 hours and adding an equal volume of PBS to the growth control group.

3. Maturation markers detection by flow cytometry: after 24 h, taking out the 6-well plate, repeatedly blowing the cells to detach them, collecting the cell suspension into a Flow Cytometry Tube, centrifuging it at 1500 rpm for 3 min, removing supernatant, adding 1 ml of PBS to continue centrifugation at 1500 rpm for 3 min, then removing the supernatant and repeatedly washing for 3 times. Adding CD11c/CD80/CD86/MHCII antibodies and incubating at room temperature for 30 min in the dark; at the same time, setting an isotype control group as the negative control group (adding isotype controls of CD11c/CD80/CD86/MHCII). After incubation, adding PBS to wash twice, then adding 200 μl of PBS to resuspend the cells, and detecting the cells by flow cytometry.

4. Result processing: analyzing the ratio of CD80/CD86/MICII in CD11c cells by flow cytometry software.

Experimental Results:

Compared with the whole-cell bacteria, the vesicles of the experimental group (MVs) treated by X-rays can significantly up-regulate the surface costimulatory molecules CD80, CD86 and MHCII of DCs after stimulation, and these surface molecules are markers of dendritic cell maturation. In conclusion, it is proved that the vesicles can significantly promote the differentiation and maturation of DCs. See FIG. 5.

Embodiment 6 of C Invention

The phagocytic ability of DC cells is detected by detecting the fluorescence intensity of FITC-dextran.

1. Culture and induction of BMDC cells.
2. Stimulation: collecting the cells on the 7th day, blowing down all the cells, then centrifuging and resuspending the cells for counting, then inoculating the cells into a 6-well plate with $1 \times 10^6$ cells per well, and respectively adding the stimulator: adding an equal volume of PBS to the GC group, adding the same concentration of membrane vesicles (by protein level) to the control group and the treatment group and then culturing them at 37° C. for 24 h.
3. Phagocytosis and detection: adding the dextran (5 μg/ml), and after culture for 1 h, aspirating the cells into a Flow Cytometry Tube; washing the cells with PBS for 3 times; adding CD11c antibody and incubating at room temperature for 30 min in the dark; washing the cells with PBS for 3 times; and detecting the fluorescence of FITC by flow cytometry.

4. Result processing: analyzing the ratio of FITC in CD11c cells by flow cytometry software.

Experimental Results:

In order to detect the phagocytic function of DCs, the present invention uses FITC-dextran as a model antigen for phagocytosis of DCs and detects the mean fluorescence intensity value of FITC of CD11c+DCs. The experimental result shows that after the DCs are stimulated by membrane vesicles, the mean fluorescence intensity value of FITC is significantly reduced compared with that of the GC group (growth control group). This experimental result proves again that the vesicles can promote the maturation of DCs, thereby reducing their ability to take up antigen. See FIG. 6.

Embodiment 7 of C Invention

Interaction between mature DCs and T cells stimulated by bacterial membrane vesicles in X-ray treatment group:

A. Interaction Between Mature DCs and CD4+T Cells:

1. Culture and induction of BMDC cells.
2. Antigen phagocytosis: culturing DCs which are cultured for 7 days in a medium containing 10 μg/ml OVA for 24 h to serve as GC (growth control group); adding vesicles to the MVs group, then centrifuging and collecting antigen-phagocytosed DCs; resuspending the DCs in a normal medium; and applying the DCs in a 96-well plate at a density of $2 \times 10^4$ cells/well, with 100 μl per well, and 3 replicate wells per group.
3. T cell extraction: on the second day, isolating and enriching OVA-specific CD4+T lymphocytes from the spleens of OT-II mice by a magnetic negative selection beads kit from Stem Cell Technologies company.
4. Co-culture of DC and T cells: labeling the sorted CD4$^+$T cells with 1 μM CFSE according to the kit instructions. After labeling, washing the cells for 3 times with PBS and adding the cells to the 96-well plate at a density of $10^5$ cells/well to a final culture volume of 200 μl (CD4:DC=5:1).
5. On the 3rd day after co-culture, detecting the proliferation of CD4+T cell population by CFSE decrement by flow cytometry.

Experimental Results:

Co-culturing membrane vesicles-stimulated and OVA-antigen-phagocytosed DCs with CFSE-labeled OT-II mouse CD4$^+$T lymphocytes in vitro. The analysis results of flow cytometry for CFSE fluorescence intensity show that the proportion of proliferating CD4$^+$T cells is increased. The membrane vesicles (14.05%) can significantly increase the proliferation-promoting effect of OVA-antigen-phagocytosed DCs (6.80%) on specific CD4$^+$T cells. See FIG. 7 and FIG. 8 for details.

B. Promotion of T Cell Proliferation by DCs Treated by the Membrane Vesicles:

1. Culture and induction of BMDC cells.
2. Antigen phagocytosis: culturing DCs which are cultured for 7 days in a medium for 24 h to serve as GC (growth control group); adding vesicles to the MVs group, then centrifuging and collecting antigen-phagocytosed DCs; resuspending the DCs in a normal medium; and applying the DCs in a 96-well plate at a density of $4 \times 10^4$ cells/well, with 100 μl per well, and 3 replicate wells per group.
3. T cell extraction: on the second day, isolating and enriching the T cells of the mice from the spleens of mice one week after one MVs immunization using a magnetic negative selection beads kit from Stem Cell Technologies company.

4. Co-culture of DC and T cells: labeling the sorted T cells with 1 μM CFSE according to the kit instructions. After labeling, washing the cells for 3 times with PBS and adding the cells to the 96-well plate at a density of $4 \times 10^5$ cells/well to a final culture volume of 200 μl (CD3:DC=10:1).

5. On the 3rd day after co-culture, detecting the proliferation of $CD3^+$, $CD8^+$ and $CD4^+T$ cell populations by CFSE decrement by flow cytometry.

Experimental Results:

Co-culturing membrane vesicles-stimulated and OVA-antigen-phagocytosed DCs with CFSE-labeled OT-II mouse $CD4^+T$ lymphocytes in vitro. The analysis results of flow cytometry for CFSE fluorescence intensity show that the proportion of proliferating $CD4^+T$ cells is increased. As shown in the figure, the fluorescence intensity of the whole-cell bacteria plus vesicle stimulation group is 63.5%, and the fluorescence intensity of the vesicle stimulation group is 71%. It indicates that DCs after vesicle treatment can significantly stimulate the proliferation of $CD4^+T$ cells. See FIG. 9.

D Invention: A Production System and an Isolation and Purification System for Bacterial Membrane Vesicles D invention relates to the field of biotechnology, and particularly relates to a production system and an isolation and purification system for bacterial membrane vesicles.

In view of the problems of modern technology in the preparation and purification of bacterial membrane vesicles, D invention provides a production system and a purification system for bacterial membrane vesicles, which are easy for industrial use.

A production system for bacterial membrane vesicles, wherein the production system is provided with a fermentation unit 1 and an irradiation unit 2 in sequence, the fermentation unit 1 is composed of a bacterial fermenter 3 and an ultraviolet spectrophotometer 4, and the irradiation unit 2 is composed of irradiation equipment 5.

The fermenter provided by D invention is suitable for fermentation of various bacteria, including gram-positive bacteria and gram-negative bacteria.

The ultraviolet spectrophotometer provided by D invention is used for accurately measuring the content of bacteria in a bacterial solution.

Further, the fermenter 3 is a ventilated fermenter, a bubbling fermenter, an airlift fermenter or a nozzle circulation fermenter.

Further, a ray generator in the irradiation equipment 5 is an X-ray generator, a γ-ray generator or a $Co^{60}$ isotope generator.

Another purpose of D invention is to provide a purification system for bacterial membrane vesicles.

A purification system for bacterial membrane vesicles, wherein the purification system is provided with a fermentation unit 1, an irradiation unit 2 and separation (isolation) equipment 6 in sequence, the fermentation unit 1 is composed of a bacterial fermenter 3 and an ultraviolet spectrophotometer 4, and the irradiation unit 2 is composed of irradiation equipment 5.

Further, the separation equipment 6 comprises a centrifugal unit 7, a dialysis bag concentration unit and/or a column chromatography unit.

Further, the fermenter 3 is a ventilated fermenter, a bubbling fermenter, an airlift fermenter or a nozzle circulation fermenter.

Further, a ray generator in the irradiation equipment 5 is an X-ray generator, a γ-ray generator or a $Co^{60}$ isotope generator.

Further, the separation equipment 6 comprises a centrifugal unit 7, and the centrifugal unit 7 is an ordinary centrifuge, a high-speed centrifuge or an ultra-high-speed centrifuge.

Another purpose of D invention is to provide a separation system for bacterial membrane vesicles.

A separation system for bacterial membrane vesicles, wherein the separation system is provided with a fermentation unit 1 and separation equipment 6 in sequence and the fermentation unit 1 is composed of a bacterial fermenter 3 and an ultraviolet spectrophotometer 4.

Further, the separation equipment 6 comprises a centrifugal unit 7, a dialysis bag concentration unit and/or a column chromatography unit.

Further, the fermenter 3 is a ventilated fermenter, a bubbling fermenter, an airlift fermenter or a nozzle circulation fermenter.

Further, the separation equipment 6 comprises a centrifugal unit 7, and the centrifugal unit 7 is an ordinary centrifuge, a high-speed centrifuge or an ultra-high-speed centrifuge.

Embodiment 1 of D Invention

Figure 10:
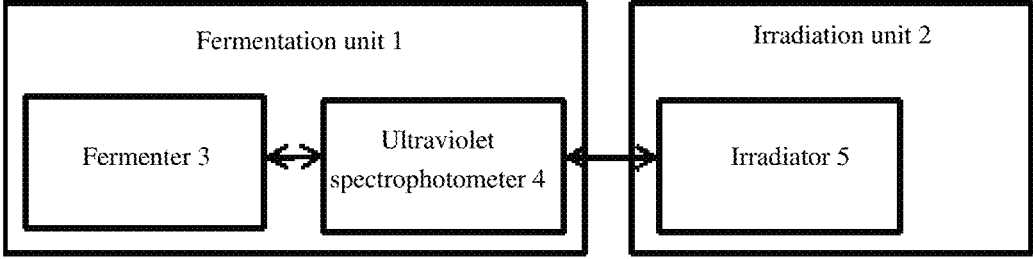
FIG. 10 is a structural schematic diagram of a production system for bacterial membrane vesicles.

See FIG. 10. Specifically, a production system of the embodiment of D invention is provided with a fermentation unit 1 and an irradiation unit 2 in sequence, the fermentation unit 1 is composed of a bacterial fermenter 3 and an ultraviolet spectrophotometer 4, and the irradiation unit 2 is composed of irradiation equipment 5. The fermenter 3 is a ventilated fermenter, a bubbling fermenter, an airlift fermenter or a nozzle circulation fermenter. A ray generator in the irradiation equipment 5 is an X-ray generator, a γ-ray generator or a $Co^{60}$ isotope generator.

In the embodiment of D invention, gram-positive bacteria and gram-negative bacteria are first fermented in the fermenter 3, then the content of bacteria in a bacterial solution is accurately controlled by the ultraviolet spectrophotometer 4 to be within a certain limit, and the fermented bacterial solution is irradiated by the irradiation equipment 5 to facilitate the bacteria to produce a large amount of MVs, thus increasing the content of MVs.

Embodiment 2 of D Invention

Figure 11:
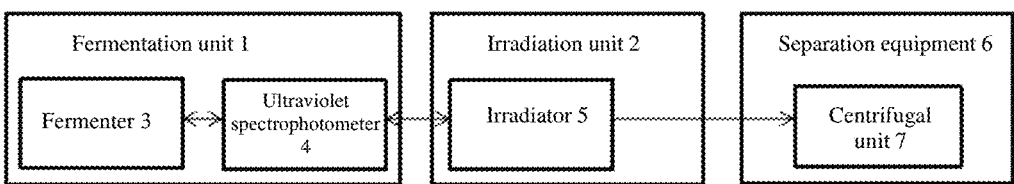
FIG. 11 is a structural schematic diagram of a purification system for bacterial membrane vesicles.

See FIG. 11. Specifically, a production system of the embodiment of D invention is provided with a fermentation unit 1, an irradiation unit 2 and separation equipment 6 in sequence, the fermentation unit 1 is composed of a bacterial fermenter 3 and an ultraviolet spectrophotometer 4, the irradiation unit 2 is composed of irradiation equipment 5, and the separation equipment 6 is composed of a centrifugal unit 7, a dialysis bag concentration unit and/or a column chromatography unit.

In the embodiment of D invention, gram-positive bacteria and gram-negative bacteria are first fermented in the fermenter 3, then the content of bacteria in a bacterial solution is accurately controlled by the ultraviolet spectrophotometer 4 to be within a certain limit, the fermented bacterial solution is irradiated by the irradiation equipment 5, the irradiated bacterial solution is further centrifuged by the centrifugal unit 7 to remove fermentation wastewater, bacterial flagella and bacterial secretions in sequence, and finally precipitation is performed to obtain membrane vesicles, i.e., purified membrane vesicles.

In the embodiment of D invention, a ray generator of the irradiation equipment is an X-ray generator, a γ-ray generator or a Co$^{60}$ isotope generator.

In the embodiment of D invention, the fermenter 3 is a ventilated fermenter, a bubbling fermenter, an airlift fermenter or a nozzle circulation fermenter.

In the embodiment of D invention, the centrifugal unit 7 includes a centrifuge, a high-speed centrifuge or an ultra-high-speed centrifuge.

Embodiment 3 of D Invention

Figure 12:
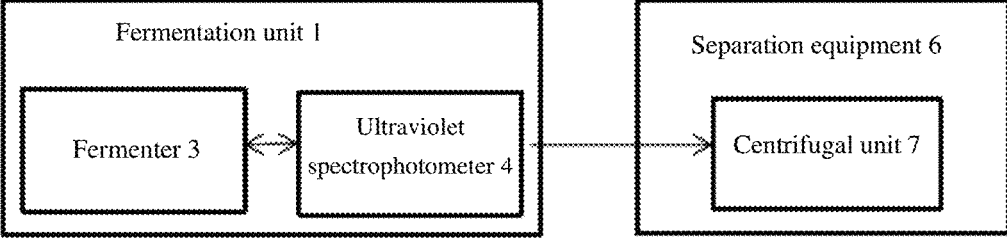
FIG. 12 is a structural schematic diagram of an isolation system for bacterial membrane vesicles.

See FIG. 12. Specifically, a separation system of the embodiment of D invention is provided with a fermentation unit 1 and separation equipment 6 in sequence, the fermentation unit 1 is composed of a bacterial fermenter 3 and an ultraviolet spectrophotometer 4, and the separation equipment 6 is composed of a centrifugal unit 7.

In the embodiment of D invention, gram-positive bacteria and gram-negative bacteria are first fermented in the fermenter 3, and then wastes such as fermentation wastewater, bacterial flagella and bacterial secretions are removed by the centrifugal unit 7 in sequence.

In the embodiment of D invention, the fermenter 3 is a ventilated fermenter, a bubbling fermenter, an airlift fermenter or a nozzle circulation fermenter.

In the embodiment of D invention, the centrifugal unit 7 includes a centrifuge, a high-speed centrifuge or an ultra-high-speed centrifuge.

E Invention: A Production System and an Isolation and Purification System and Method for Bacterial Membrane Vesicles E invention relates to the field of biotechnology, and particularly relates to a production system and method for bacterial membrane vesicles, and an isolation and purification system and method for bacterial membrane vesicles.

Based on the problems of modern technology in the production, preparation and purification of bacterial membrane vesicles, E invention provides a system and method for increasing yield of bacterial MVs as well as a system and method for purifying bacterial MVs. For the technology adopted in the present invention, no chemical irritant substances are added, so no adverse effect is caused. At the same time, the technical process is simple with high vesicle yield, high efficiency and good amplification effect; and can be used for large-scale preparation of vesicles.

The purpose of E invention is to provide a production system for bacterial membrane vesicles.

A production system for bacterial membrane vesicles, wherein the production system is provided with a fermentation unit 1 and an irradiation unit 2 in sequence, the fermentation unit 1 is composed of a bacterial fermenter 3 and an ultraviolet spectrophotometer 4, and the irradiation unit 2 is composed of irradiation equipment 5.

Further, the fermenter 3 is a ventilated fermenter, a bubbling fermenter, an airlift fermenter or a nozzle circulation fermenter.

Further, a ray generator in the irradiation equipment 5 is an X-ray generator, a γ-ray generator or a Co$^{60}$ isotope generator.

The purpose of E invention is also to provide a production method for bacterial membrane vesicles.

A method for producing bacterial membrane vesicles by the above production system, comprising the following steps:
   1) Culturing bacteria to logarithmic growth phase, and performing fermentation to further enrich the bacteria;

2) Collecting bacterial cells, resuspending the bacterial cells with an appropriate amount of phosphate buffer solution or sterile normal saline; and
   3) Irradiating the bacterial cells with ionizing irradiation.

The bacteria of the present invention comprise gram-positive bacteria and gram-negative bacteria. The bacteria specifically include the following species:

| | |
|---|---|
| Gram-positive bacteria | *Staphylococcus aureus*, *Streptococcus*, *Corynebacterium diphtheriae*, *Mycobacterium tuberculosis*, *Clostridium tetani*, *Bacillus*, *corynebacterium* (and genetically engineered bacteria of the above bacteria), etc. |
| Gram-negative bacteria | *Pseudomonas aeruginosa*, *Acinetobacter baumannii*, *Escherichia coli*, *Salmonella typhi*, *Diplococcus meningitidis*, *Proteusbacillus vulgaris*, *Shigella* (and genetically engineered bacteria of the above bacteria), etc. |

Further, $OD_{600}$ value of the bacteria in logarithmic growth phase in the step 1) is 0.3-0.8; and the ratio of the amount of the phosphate buffer solution or sterile normal saline added in the step 2) to the total amount of the bacterial cells is that the amount of the bacteria contained in every 1 ml of solution is $OD_{600}$ value of 20-80.

Preferably, the $OD_{600}$ value of the bacteria in logarithmic growth phase in the step 1) is 0.5-0.8; and the ratio of the amount of the phosphate buffer solution or sterile normal saline added in the step 2) to the total amount of the bacterial cells is that the amount of the bacteria contained in every 1 ml of solution is $OD_{600}$ value of 40-60.

Further, the irradiation in the step 3) is X-rays, and an irradiation dose range is 500-3000 Gy. The irradiation dose specifically comprises: 500-600 Gy, 600-700 Gy, 700-800 Gy, 800-900 Gy, 900-1000 Gy, 1000-1100 Gy, 1100-1200 Gy, 1200-1300 Gy, 1300-1400 Gy, 1400-1500 Gy, 1500-1600 Gy, 1600-1700 Gy, 1700-1800 Gy, 1800-1900 Gy, 1900-2000 Gy, 2100-2200 Gy, 2200-2300 Gy, 2300-2400 Gy, 2400-2500 Gy, 2500-2600 Gy, 2600-2700 Gy, 2700-2800 Gy, 2800-2900 Gy and 2900-3000 Gy.

The purpose of E invention is also to provide a purification system for bacterial membrane vesicles.

A purification system for bacterial membrane vesicles, wherein the purification system is provided with a fermentation unit 1, an irradiation unit 2 and separation equipment 6 in sequence, the fermentation unit 1 is composed of a bacterial fermenter 3 and an ultraviolet spectrophotometer 4, the irradiation unit 2 is composed of irradiation equipment 5, and the separation equipment 6 is composed of a centrifugal unit 7.

Further, the fermenter 3 is a ventilated fermenter, a bubbling fermenter, an airlift fermenter or a nozzle circulation fermenter.

Further, a ray generator in the irradiation equipment 5 is an X-ray generator, a γ-ray generator or a Co$^{60}$ isotope generator.

Further, the centrifugal unit 7 is an ordinary centrifuge, a high-speed centrifuge or an ultra-high-speed centrifuge.

The purpose of E invention is also to provide a purification method for bacterial membrane vesicles.

A method for purifying bacterial membrane vesicles by the above purification system, comprising the following steps:
   1) Culturing bacteria to logarithmic growth phase, and performing fermentation to further enrich the bacteria;
   2) Collecting bacterial cells, resuspending the bacterial cells with an appropriate amount of phosphate buffer solution or sterile normal saline, and irradiating the bacterial cells with ionizing irradiation;

3) Collecting the irradiated bacterial solution, centrifuging the bacterial solution, discarding supernatant, and filtering the supernatant with a 0.3-0.5 µM filter to remove the bacteria;

4) Centrifuging the filtered supernatant with a high-speed centrifuge, collecting the supernatant, and removing flagella;

5) Centrifuging the supernatant after removing the flagella at an ultra-high speed to precipitate membrane vesicles; and 6) Collecting the purified membrane vesicles.

Further, $OD_{600}$ value of the bacteria in logarithmic growth phase in the step 1) is 0.3-0.8; and the ratio of the amount of the phosphate buffer solution or sterile normal saline added in the step 2) to the total amount of the bacterial cells is that $OD_{600}$ value of the amount of the bacteria contained in every 1 ml of solution is 20-80.

Preferably, the $OD_{600}$ value of the bacteria in logarithmic growth phase in the step 1) is 0.5-0.8; and the ratio of the amount of the phosphate buffer solution or sterile normal saline added in the step 2) to the total amount of the bacterial cells is that $OD_{600}$ value of the amount of the bacteria contained in every 1 ml of solution is 40-60.

Further, the ionizing irradiation in the step 2) is X-rays, and an irradiation dose range is 500-3000 Gy. The irradiation dose specifically comprises: 500-600 Gy, 600-700 Gy, 700-800 Gy, 800-900 Gy, 900-1000 Gy, 1000-1100 Gy, 1100-1200 Gy, 1200-1300 Gy, 1300-1400 Gy, 1400-1500 Gy, 1500-1600 Gy, 1600-1700 Gy, 1700-1800 Gy, 1800-1900 Gy, 1900-2000 Gy, 2100-2200 Gy, 2200-2300 Gy, 2300-2400 Gy, 2400-2500 Gy, 2500-2600 Gy, 2600-2700 Gy, 2700-2800 Gy, 2800-2900 Gy and 2900-3000 Gy.

Further, the centrifugation speed in the step 3) is 100-10000 g, and the centrifugation time is 10-60 min.

Preferably, the centrifugation speed in the step 3) is 400-8000 g, and the centrifugation time is 10-30 min.

Further, the high-speed centrifugation speed in the step 4) is 5000-25000 g, and the high-speed centrifugation time is 10-100 min.

Preferably, the high-speed centrifugation speed in the step 4) is 10000-20000 g, and the high-speed centrifugation time is 30-60 min.

Further, the ultra-high-speed centrifugation speed in the step 5) is 5000-150000 g, and the ultra-high-speed centrifugation time is 60-600 min.

Preferably, the ultra-high-speed centrifugation speed in the step 5) is 15000-150000 g, and the ultra-high-speed centrifugation time is 60-180 min.

Embodiment 1 of E Invention

See FIG. 10. Specifically, a production system of the embodiment of E invention is provided with a fermentation unit 1 and an irradiation unit 2 in sequence, the fermentation unit 1 is composed of a bacterial fermenter 3 and an ultraviolet spectrophotometer 4, and the irradiation unit 2 is composed of irradiation equipment 5. The fermenter 3 is a ventilated fermenter, a bubbling fermenter, an airlift fermenter or a nozzle circulation fermenter. A ray generator in the irradiation equipment 5 is an X-ray generator, a γ-ray generator or a $Co^{60}$ isotope generator.

In the embodiment of E invention, gram-positive bacteria and gram-negative bacteria are first fermented in the fermenter 3, then the content of bacteria in a bacterial solution is accurately controlled by the ultraviolet spectrophotometer 4 to be within a certain limit, and the fermented bacterial solution is irradiated by irradiation through the irradiation equipment 5 to facilitate the bacteria to produce a large amount of MVs.

A method for producing bacterial membrane vesicles by the above production system, comprising the following steps:

1) Culturing bacteria to logarithmic growth phase, wherein $OD_{600}$ value of the bacteria in logarithmic growth phase is 0.3-0.8; and then performing fermentation to further enrich the bacteria;

2) Collecting bacterial cells, and resuspending the bacterial cells with an appropriate amount of phosphate buffer solution or sterile normal saline, wherein the ratio of the amount of the phosphate buffer solution or sterile normal saline added to the total amount of the bacterial cells is that the $OD_{600}$ value of the amount of the bacteria contained in every 1 ml of solution is 20-80; and 3) Irradiating the bacterial solution with X-rays, with an irradiation dose range of 500-3000 Gy. The irradiation dose optionally comprises: 500-600 Gy, 600-700 Gy, 700-800 Gy, 800-900 Gy, 900-1000 Gy, 1000-1100 Gy, 1100-1200 Gy, 1200-1300 Gy, 1300-1400 Gy, 1400-1500 Gy, 1500-1600 Gy, 1600-1700 Gy, 1700-1800 Gy, 1800-1900 Gy, 1900-2000 Gy, 2100-2200 Gy, 2200-2300 Gy, 2300-2400 Gy, 2400-2500 Gy, 2500-2600 Gy, 2600-2700 Gy, 2700-2800 Gy, 2800-2900 Gy and 2900-3000 Gy.

Embodiment 2 of E Invention

See FIG. 11. Specifically, a purification system of the embodiment of E invention is provided with a fermentation unit 1, an irradiation unit 2 and separation equipment 6 in sequence, the fermentation unit 1 is composed of a bacterial fermenter 3 and an ultraviolet spectrophotometer 4, the irradiation unit 2 is composed of irradiation equipment 5, and the separation equipment 6 is composed of a centrifugal unit 7.

In the embodiment of E invention, gram-positive bacteria and gram-negative bacteria are first fermented in the fermenter 3, then the content of bacteria in a bacterial solution is accurately controlled by the ultraviolet spectrophotometer 4 to be within a certain limit, the fermented bacterial solution is irradiated by the irradiation equipment 5, the irradiated bacterial solution is further centrifuged by the centrifugal equipment 6 to remove fermentation wastewater, bacterial flagella and bacterial secretions in sequence, and finally precipitation is performed to obtain membrane vesicles, i.e., purified membrane vesicles.

In the embodiment of E invention, a ray generator of the irradiation equipment is an X-ray generator, a γ-ray generator or a $Co^{60}$ isotope generator.

In the embodiment of E invention, the fermenter 3 is a ventilated fermenter, a bubbling fermenter, an airlift fermenter or a nozzle circulation fermenter.

In the embodiment of E invention, the centrifugal unit 7 includes a centrifuge, a high-speed centrifuge or an ultra-high-speed centrifuge.

A method for purifying bacterial membrane vesicles by the above purification system, comprising the following steps:

1) Culturing bacteria to logarithmic growth phase, wherein $OD_{600}$ value of the bacteria in logarithmic growth phase is 0.3-0.8; and performing fermentation to further enrich the bacteria;

2) Collecting bacterial cells, and resuspending the bacterial cells with an appropriate amount of phosphate buffer solution or sterile normal saline, wherein the ratio of the amount of the phosphate buffer solution or sterile normal saline added to the total amount of the bacterial cells is that $OD_{600}$ value of the amount of the bacteria contained in every 1 ml of solution is 20-80; and irradiating the resuspended bacterial solution with X-rays, with an irradiation dose range of 500-3000 Gy;

3) Collecting the irradiated bacterial solution at the centrifugation speed of 100-10000 g for the centrifugation time of 10-60 min; discarding supernatant after centrifugation, and filtering the supernatant with a 0.45 μM filter to remove the bacteria;

4) Centrifuging the supernatant after removing the bacteria with a high-speed centrifuge, wherein the high-speed centrifugation speed is 5000-25000 g, and the high-speed centrifugation time is 10-100 min; collecting the supernatant, and removing flagella;

5) Centrifuging the supernatant after removing the flagella at an ultra-high speed, wherein the ultra-high speed centrifugation speed is 5000-150000 g, and the ultra-high-speed centrifugation time is 60-600 min; precipitating membrane vesicles; and 6) Collecting the membrane vesicles after optimized production.

The embodiments of the present invention are described above in combination with drawings, but the present invention is not limited to the aforementioned specific embodiments. The aforementioned embodiments are merely illustrative and not limiting. For those of ordinary skill in the art, many forms can be made under the teaching of present invention without departing from the spirit of the present invention and the scope of the claims, all of which shall fall within the protection scope of the present invention.

REFERENCE

Beveridge T J. Structures of gram-negative cell walls and their derived membrane vesicles [J]. Journal of bacteriology, 1999, 181(16): 4725-4733.

Kulp A, Kuehn M J. Biological functions and biogenesis of secreted bacterial outer membrane vesicles [J]. Annual review of microbiology, 2010, 64 (163-184).

Devos S, Van Oudenhove L, Stremersch S, Van Putte W, De Rycke R, et. al. The effect of imipenem and diffusible signaling factors on the secretion of outer membrane vesicles and associated Ax21 proteins in *Stenotrophomonas maltophilia* [J]. Frontiers in Microbiology, 2015 vol: 6 pp: 298.

The invention claimed is:

1. A method for preparing membrane vesicles of bacteria, wherein the bacteria comprise *Pseudomonas aeruginosa* or *Staphylococcus aureus*, and the method comprises the following steps:
    Step 1) Culturing the bacteria to logarithmic growth phase;
    Step 2) Collecting bacterial cells, resuspending the bacterial cells to obtain a bacterial solution, and irradiating the bacterial solution with ionizing irradiation to obtain irradiated bacterial solution, wherein the ionizing irradiation is X-rays, and irradiation dose is 500-1000 Gy;
    Step 3) Collecting the irradiated bacterial solution, centrifuging the irradiated bacterial solution at 100-10000 g for 10-60 min, collecting supernatant 1, and filtering the supernatant 1 with a 0.3-0.5 μM filter to remove the bacterial cells and obtain filtered supernatant 1;
    Step 4) Centrifuging the filtered supernatant 1 at 5000-25000 g for 10-100 min, collecting supernatant 2;
    Step 5) Centrifuging the supernatant 2 at 5000-150000 g for 60-600 min to precipitate and obtain the membrane vesicles.

2. The method according to claim 1, wherein $OD_{600}$ value of the bacteria in logarithmic growth phase in the step 1) is 0.3-0.8.

3. The method according to claim 1, wherein the bacterial cells were resuspended with phosphate buffer solution or sterile normal saline in the step 2), and $OD_{600}$ value of the bacterial solution is 20-80.

4. The method according to claim 1, wherein the supernatant 1 in the step 3) is filtered with a 0.45 μM filter to remove the bacterial cells.

5. The method according to claim 1, wherein the method is conducted using a production system, wherein the production system is provided with a fermentation unit 1 and an irradiation unit 2 arranged to be connected in sequence, the fermentation unit 1 comprises a bacterial fermenter 3 and an ultraviolet spectrophotometer 4, and the irradiation unit 2 comprises an irradiation equipment 5.

6. The method according to claim 5, wherein the bacterial fermenter 3 is a ventilated fermenter, a bubbling fermenter, an airlift fermenter, or a nozzle circulation fermenter.

7. The method according to claim 5, wherein the irradiation equipment 5 comprises an X-ray generator.

8. The method according to claim 5, wherein the irradiation unit 2 is further connected to a separation equipment 6.

9. The method according to claim 8, wherein the separation equipment 6 comprises a centrifugal unit 7.

\* \* \* \* \*